US008703201B2

(12) United States Patent
Belzer et al.

(10) Patent No.: US 8,703,201 B2
(45) Date of Patent: Apr. 22, 2014

(54) HYPERPOLARIZATION METHODS, SYSTEMS AND COMPOSITIONS

(75) Inventors: Avrum Belzer, Brookline, MA (US); Neal Kalechofsky, Stow, MA (US)

(73) Assignee: Millikelvin Technologies LLC, Braintree, MA (US)

(*) Notice: Subject to any disclaimer, the term of this patent is extended or adjusted under 35 U.S.C. 154(b) by 0 days.

(21) Appl. No.: 13/335,076

(22) Filed: Dec. 22, 2011

(65) Prior Publication Data

US 2012/0114851 A1  May 10, 2012

Related U.S. Application Data

(63) Continuation of application No. 12/193,536, filed on Aug. 18, 2008, now abandoned, which is a continuation of application No. PCT/US2007/004654, filed on Feb. 21, 2007.

(60) Provisional application No. 60/775,196, filed on Feb. 21, 2006, provisional application No. 60/802,699, filed on May 23, 2006.

(51) Int. Cl.
*A61K 49/06* (2006.01)
*A61K 49/08* (2006.01)
*A61K 49/18* (2006.01)
*A61B 5/055* (2006.01)
*G01N 24/08* (2006.01)
*G01R 33/20* (2006.01)

(52) U.S. Cl.
USPC .......................................... 424/489; 424/9.3

(58) Field of Classification Search
None
See application file for complete search history.

(56) References Cited

U.S. PATENT DOCUMENTS

| | | | |
|---|---|---|---|
| 5,565,215 A * | 10/1996 | Gref et al. ...................... 424/501 |
| 5,617,859 A | 4/1997 | Souza et al. |
| 6,453,188 B1 | 9/2002 | Ardenkjaer-Larsen et al. |
| 6,466,814 B1 * | 10/2002 | Ardenkjaer-Larsen et al. ............... 600/420 |
| 6,471,993 B1 | 10/2002 | Shastri et al. .................. 424/486 |
| 6,651,459 B2 | 11/2003 | Kalechofsky |
| 2003/0017110 A1 * | 1/2003 | Pines et al. ...................... 424/9.6 |
| 2003/0120470 A1 | 6/2003 | Korzekwa et al. |
| 2003/0121279 A1 * | 7/2003 | Kalechofsky .................. 62/601 |
| 2003/0185760 A1 * | 10/2003 | Lanza et al. ............... 424/9.321 |
| 2003/0189182 A1 * | 10/2003 | Hasson et al. ............. 251/129.2 |
| 2005/0187398 A1 | 8/2005 | Bell et al. |
| 2005/0200356 A1 | 9/2005 | Hennig |
| 2006/0124510 A1 | 6/2006 | Kalechofsky |
| 2006/0173282 A1 | 8/2006 | Ardenkjaer-Larsen et al. |
| 2007/0156046 A1 | 7/2007 | Hasing et al. |
| 2008/0000471 A1 | 1/2008 | Bolam et al. |

FOREIGN PATENT DOCUMENTS

| | | |
|---|---|---|
| EP | 1548454 A1 | 6/2005 |
| WO | WO-91/12024 | 8/1991 |
| WO | WO-95/27438 | 10/1995 |
| WO | WO-96/40585 | 12/1996 |
| WO | 97 37239 A1 | 10/1997 |
| WO | WO-97/37177 | 10/1997 |
| WO | WO-97/37178 | 10/1997 |
| WO | WO-98/01766 | 1/1998 |
| WO | WO-98/58272 | 12/1998 |
| WO | WO-99/07415 | 2/1999 |
| WO | WO-99/24080 | 5/1999 |
| WO | WO-99/34189 | 7/1999 |
| WO | WO-99/35508 | 7/1999 |
| WO | 99/66255 A2 | 12/1999 |
| WO | WO-99/66254 | 12/1999 |
| WO | WO-01/11285 | 2/2001 |
| WO | WO-02/36005 | 5/2002 |
| WO | WO-02/37132 | 5/2002 |
| WO | WO-2006/079702 | 8/2006 |
| WO | WO 2007007022 A1 * | 1/2007 |
| WO | WO-2007136439 A2 | 11/2007 |
| WO | WO-2009146153 A2 | 12/2009 |
| WO | WO-2011026103 A2 | 3/2011 |

OTHER PUBLICATIONS

V Callot, E Canet, J Brochot, D Dupuich, H Humblot, A Briguet, H Tournier, Y Cremillieux. "On the feasibility of tissue perfusion quantification using hyperpolarized encapsulated helium3." Proceedings of the International Society for Magnetic Resonance in Medicine, vol. 10, 2002, 1 page.*
The Engineering Toolbox. "Solubility of Gases in Water." http://www.engineeringtoolbox.com/gases-solubility-water-d_1148.html, accessed May 28, 2013, 6 printed pages.*
CN-200720011444.3—Office Action, Aug. 30, 2010, Kalechofsky.
CN-200780011444.3—English Translation of Office Action, Aug. 30, 2010, Kalechofsky, one page only.
PCT-US2010-047310—International Search Report and Written Opinion, May 30, 2011, Millikelvin Technologies LLC et al.
PCT-US2009-039696—International Preliminary Report on Patentability with Written Opinion of the International Searching Authority (ISA), Nov. 17, 2009, Millikelvin Technologies LLC et al.
Research News Berkeley Lab; Hyper-Crest MRI Breaks New Ground in Molecular Imaging, Oct. 19, 2006.
APS Water Presentation; Mar. 5-9, 2007, Denver; http://www.aps.org/meetings/march.
International Search Report and the Written Opinion of the International Searching Authority dated Nov. 17, 2009.
"Enhancement of Solution NMR and MRI with Laser-Polarized Xenon," Navon, G., Song, Y.-Q., Rõõm, T., Appelt, S., Taylor, R. E. and Pines, A., (1996). Science 271, 1848.
"Polarization Transfer using Hyperpolarized Supercritical Xenon," Jason C. Leawoods, Brian T. Saam, and Mark S. Conradi, Chem. Phys. Lett. 327, 359-364 (2000).

(Continued)

*Primary Examiner* — Frederick Krass
*Assistant Examiner* — Isaac Shomer
(74) *Attorney, Agent, or Firm* — Brian R. Pollack; Day Pitney LLP

(57) ABSTRACT

The disclosure provides various methods and systems for providing hyperpolarized materials as well as the hyperpolarized materials so provided. In addition, methods of providing hyperpolarized materials, such as agents, to end users from a remote location are also provided.

22 Claims, 12 Drawing Sheets

(56) References Cited

OTHER PUBLICATIONS

"Increase in signal-to-noise ratio of > 10,000 times in liquid-state NMR" Jan H. Ardenkjeer-Larsen, Björn Fridlund, Andreas Gram, Georg Hansson, Lennart Hansson, Mathilde H. Lerche, Rolf Servin, Mikkel Thaning, and Klaes Golman, Proc Natl Acad Sci U S A. Sep. 2, 2003; 100(18): 10158-10163.

"Polarization of $^3$He, $D_2$ (and possibly $^{129}$Xe) using cryogenic techniques" G. Frossati, Nuclear Instruments and Methods in Physics Research Section A: Accelerators, Spectrometers, Detectors and Associated Equipment; vol. 402, Issues 2-3, Jan. 11, 1998, pp. 479-483.

"In vivo magnetic resonance vascular imaging using laser-polarized 3He microbubbles" Mark S. Chawla, X. Josette Chen, Harald E. Moller, Gary P. Cofer, C. Ted Wheeler, Laurence W. Hedlund, and G. Allan Johnson, Proc. Natl. Acad. Sci. USA vol. 95, pp. 10832-10835, Sep. 1998 Medical Sciences.

Database Dissabs [Online] 2002, Leawoods, Jason Clay [Ph.D.]: "Novel applications of hyperpolarized gases", XP002686426, retrieved from STN accession No. 2003:25572 Database accession No. AAI3065066 & Leawoods, Jason Clay: "Novel applications of hyperpolarized gases: Abstract of Ph. D. thesis", Dissertation Abstracts International, vol. 63, No. 9B, 2002, p. 4225, Washington University, US ISBN: 0-493-84267-5.

Duhamel G et al: "In vivo <129>Xe NMR in rat brain during intra-arterial injection of hyperpolarized <129>Xe dissolved in a lipid emulsion", Comptes Rendus Des Seances De L'Academie Des Sciences.Serie III: Sciences De La Vie, vol. 323, No. 6, Jun. 1, 2000, pp. 529-536, XP004330638, ISSN: 0764-4469, DOI: 10.1016/S0764-4469(00)00147-5.

Krjukov E V et al: "Brute Force Polarization of 129Xe", Journal of Low Temperature Physics, vol. 140, No. 5-6, Sep. 1, 2005, pp. 397-408, XP019282982, ISSN: 1573-7357.

European Search Opinion and Supplementary Search Report for corresponding EP application No. EP 07088986.9, date of completion: Nov. 5, 2012.

Notification of Reasons for Refusal issued in corresponding Japanese patent application No. 2008-556426, Sep. 3, 2013 (in the English and Japanese languages).

Verhulst, "Optical Pumping Experiments to Increase the Polarization in Nuclear-Spin Based Quantum Computers", Dissertation, Dec. 2004.

Office Action mailed Jan. 13, 2014 in co-pending related Canadian Application No. 2,643,306, citing References D1, D2, D3, D4 and D5 previously submitted in IDS filed on Apr. 17, 2013 in this application in connection with Opinion and Search Report for co-pending related European Application No. 07088986.9.

\* cited by examiner

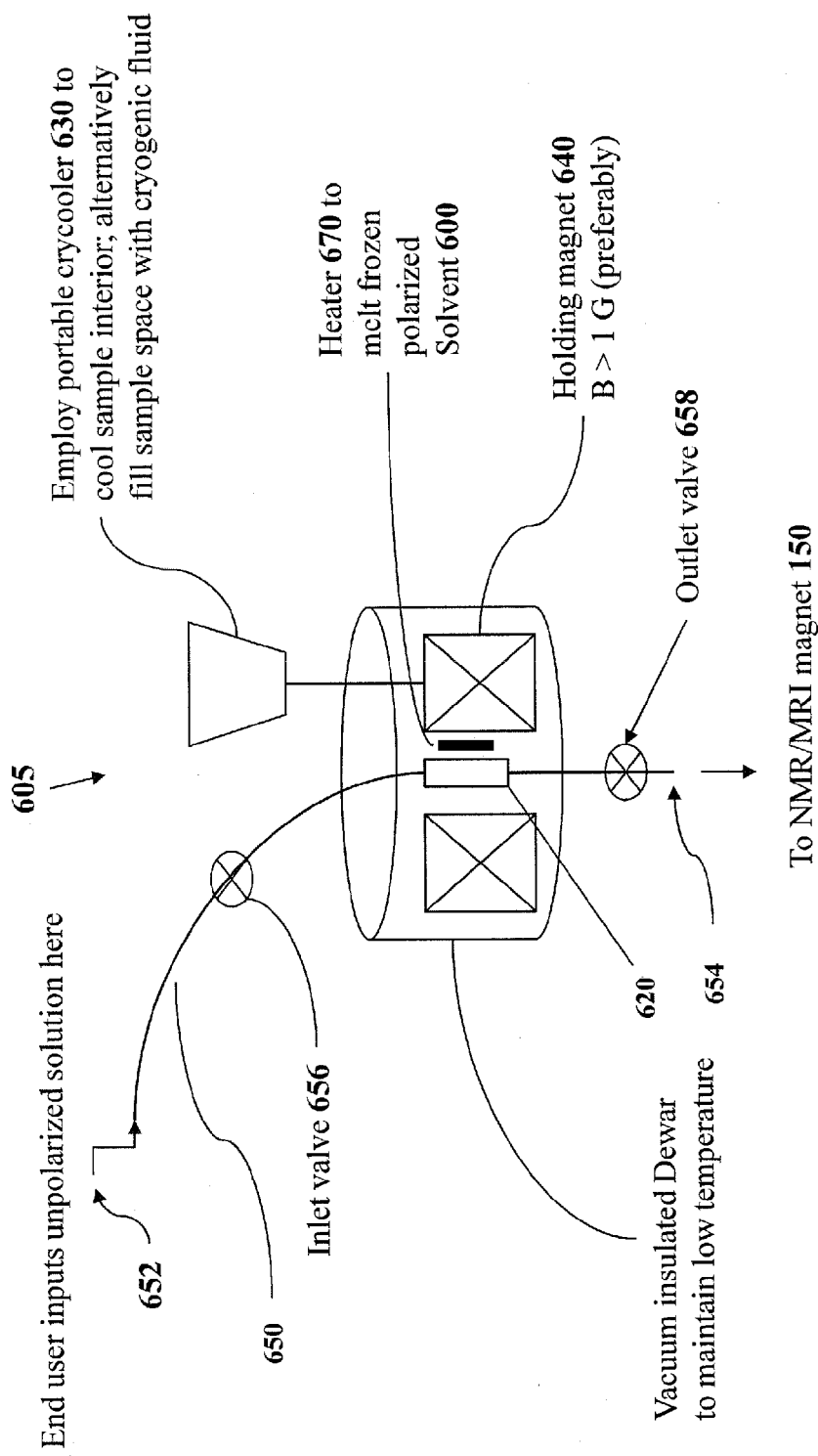

Select an agent 720 for use as MR tracer

Encapsulate agent 720 in polymer shells 710

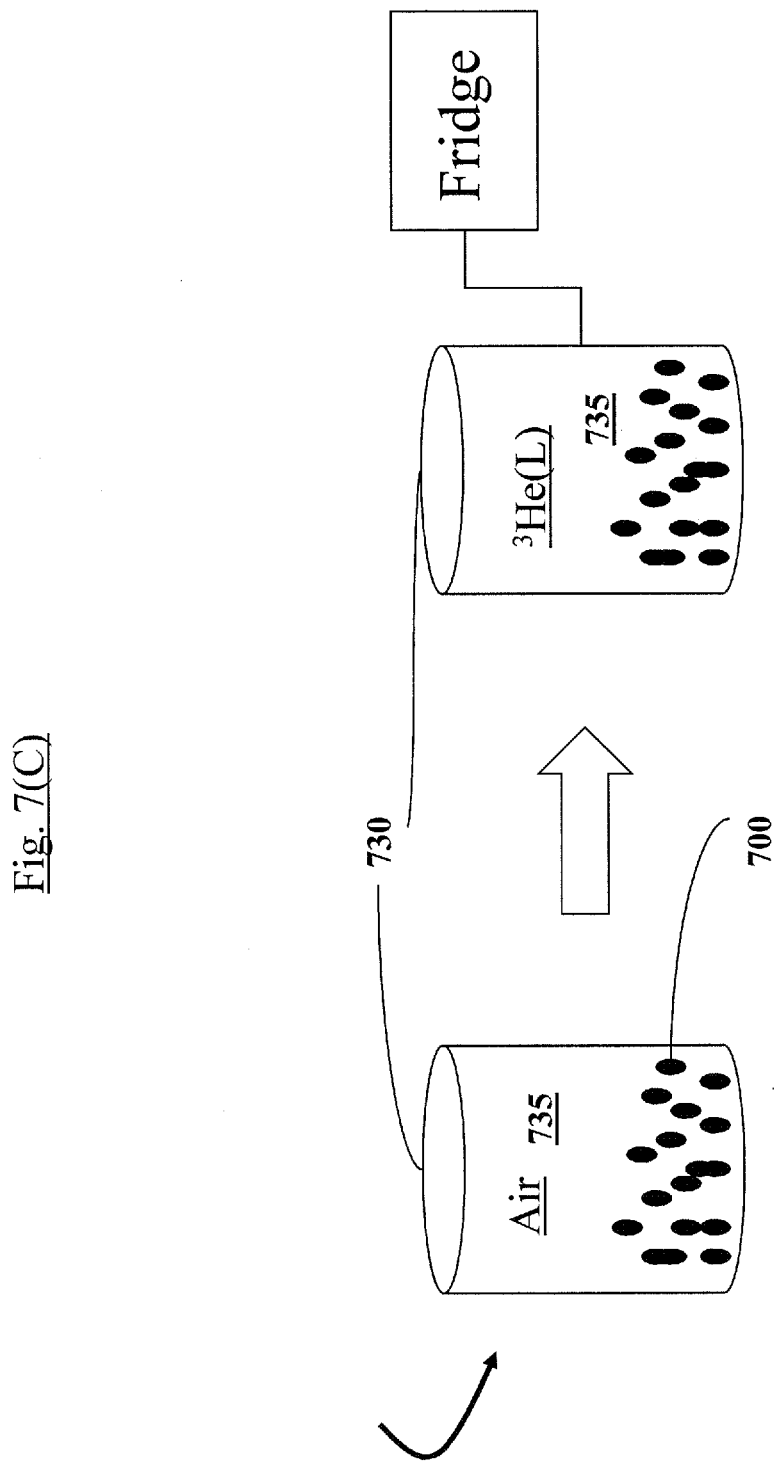

Agent 720 freezes and contracts away from polymer shell 710, leaving a gap 740

³He relaxes nuclei in agent 720 to facilitate high polarization condition.

HYPERPOLARIZATION METHODS, SYSTEMS AND COMPOSITIONS

CROSS-REFERENCE TO RELATED APPLICATIONS

This application claims the benefit of priority from and is a continuation of U.S. patent application Ser. No. 12/193,536, filed Aug. 18, 2008, which in turn claims the benefit of priority to and is a continuation of International Application No. PCT/US2007/004654, filed Feb. 21, 2007, which in turn claims the benefit of priority of U.S. Provisional Patent Application Ser. No. 60/775,196 filed Feb. 21, 2006 and U.S. Provisional Patent Application Ser. No. 60/802,699 filed May 23, 2006. The disclosure of each of the aforementioned patent applications is incorporated by reference herein in its entirety for any purpose whatsoever.

BACKGROUND OF THE INVENTION

1. Field of the Invention

The present invention relates to hyperpolarization methods, systems and compositions of hyperpolarizable materials suitable for various applications. Particularly, the present invention is directed to hyperpolarization methods, systems and compositions that facilitate magnetic resonance imaging ("MRI") and nuclear magnetic resonance ("NMR") analysis.

2. Description of Related Art

A variety of techniques are known in the art for providing hyperpolarization. Many of these techniques are directed to providing hyperpolarized noble gases. The use of a hyperpolarized noble gas, for example, can be advantageous in performing MRI or NMR as it can dramatically increase the signal to noise ratio ("SNR") in MRI or NMR procedures. This permits MRI and NMR to be used to analyze regions of interest in unprecedented ways.

To date the emphasis in the literature has been on providing complex and expensive systems for hyperpolarization. While these systems have been generally satisfactory for the purpose for which they were intended, such systems still do not solve numerous problems in the art. For example, use of these systems has generally been limited to only those facilities and researchers that can afford such expensive and complex systems, which typically cost hundreds of thousands of dollars, or more.

Similarly, some efforts have been made at providing hyperpolarized materials to transfer hyperpolarization to targets of interest. To date these efforts have focused on hyperpolarized xenon as a solvent for NMR analysis applications. For example, in Navon, G., Song, Y.-Q., Rõõm, T., Appelt, S., Taylor, R. E. and Pines, A., (1996). *Science* 271, 1848, the disclosure of which is incorporated by reference in its entirety herein, hyperpolarized xenon gas was liquefied and used as a solvent; transfer of polarization to several dissolved species was demonstrated. In a similar work, Polarization Transfer using Hyperpolarized Supercritical Xenon," Jason C. Leawoods, Brian T. Saam, and Mark S. Conradi, Chem. Phys. Lett. 327, 359-364 (2000), supercritical xenon (($P>5.83$ MPa, $T>290$ K) was employed as a solvent and transfer of polarization to several solutes was achieved.

However, xenon is very unsatisfactory as a solvent as highly specialized physical conditions are necessary for most materials of interest to dissolve in it. These conditions are not ones that lend themselves to the great bulk of actual NMR/MRI studies. There is therefore a need in the art for a method that can provide hyperpolarized materials suitable for use at standard conditions.

In U.S. Pat. No. 6,466,814, a method of producing a hyperpolarized solution is described wherein a high T1 agent is first polarized and then dissolved in a solvent. This method has the drawback that the polarization is limited by the T1 of the agent. There is therefore a significant need in the art for new methods of manufacturing hyperpolarized solutions.

There is a also significant need in the art for hyperpolarization systems, methods and compositions that reduce the cost of obtaining hyperpolarized material, and increase the practicality of using hyperpolarized material to enhance MRI and NMR. The present invention provides solutions for these and other problems, as described herein.

SUMMARY OF THE INVENTION

The purpose and advantages of the present invention will be set forth in and become apparent from the description that follows. Additional advantages of the invention will be realized and attained by the methods and systems particularly pointed out in the written description and claims hereof, as well as from the appended drawings.

To achieve these and other advantages and in accordance with a first aspect of the invention, a method of producing a hyperpolarized material is provided. The method includes providing a first material that is a liquid or a non-noble gas at standard conditions, increasing the nuclear hyperpolarization of the first material until the first material becomes hyperpolarized, and subsequently transferring the nuclear hyperpolarization from the first material to a second material or other materials, as desired.

In accordance with a further aspect the first material can also include solid material. The first material may be mixed with the second material to create a mixture, such as (i) a solution, (ii) a suspension, (iii) an emulsion, (iv) a colloid, or (v) a composite material at standard conditions suitable for use in an NMR study and/or suitable for injection in vivo. In accordance with one embodiment, nuclear hyperpolarization may be transferred from the first material to the second material via thorough mixing. For example, the second material may be dissolved in the first material. In accordance with another embodiment, nuclear hyperpolarization may be transferred from the first material to the second material by way of electromagnetic coupling. For example, the electromagnetic coupling may be provided by electromagnetic pulse sequences. The first material may then be removed or it may be retained depending on the desired application.

By way of further example, the second material may first be hyperpolarized instead of the first material. By way of still further example, the first and second material may be mixed together and then be hyperpolarized. By way of still further example, a mixture of more than two materials (such as three, four, five, six or more materials) may be provided, wherein one or more of the materials may be hyperpolarized before they are introduced into the mixture. By way of further example, a subset of the materials may be hyperpolarized and then mixed with the remaining materials. Moreover, if desired, all of the materials may be hyperpolarized at the same time. Moreover, if desired, materials as described herein may be hyperpolarized while they are being mixed.

In accordance with a further aspect, the first material and/or second material may be suitable for in vitro NMR analysis. Preferably, for in vitro NMR analysis purposes, the first material is selected from a group of materials commonly used as solvents in NMR studies such as water, saline solution, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof. Moreover, at least one of the first material and/or second material may include a physiologically tolerable liquid suitable for use in in vivo MRI studies.

For in vivo MRI purposes, the first material is preferably selected from a group of materials commonly used for injection of in vivo solutions and/or suspensions such as water, deuterated water, other FDA approved liquids, and the like. In accordance with yet another aspect, the method may further include performing an analysis of a region proximate the target material and/or the target material itself. For example, the analysis may include forming magnetic resonance images of a region of interest such as of a patient. By way of further example, the analysis may include analyzing NMR spectra of an in vitro or in vivo sample, such as a target or targets.

A system for producing a hyperpolarized material is also provided herein. The system includes a means for providing a first material, where the first material is a liquid, a solid or a non-noble gas at standard conditions, a means for increasing the nuclear polarization of the first material until the first material becomes hyperpolarized, and means for transferring the hyperpolarization from the first material to a second material.

The invention also provides a method of hyperpolarizing a material, including providing an object having a solid surface, the solid surface including hyperpolarized material. The method further includes transferring hyperpolarization from the hyperpolarized material to a fluid in contact with the solid surface.

In accordance with a further aspect, the object may be spherical in shape, or have any other suitable shape. Moreover, the solid surface may include material containing nuclei selected from the group including $^{13}C$, $^{15}N$, $^{1}H$, $^{2}H$, $^{31}P$, $^{19}F$, $^{29}Si$ and combinations thereof, among others. In accordance with one embodiment, the fluid may be a liquid. For example, the liquid may be selected from the group commonly used as solvents in NMR studies including water, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof. In accordance with another aspect, the fluid may be a gas. The gas may be selected from those commonly used for inhalation therapy purposes including, for example, air, nitrogen, carbon dioxide, xenon, $^{3}He$, and combinations thereof, among others.

In further accordance with the invention, an apparatus for transferring hyperpolarization is provided. The apparatus includes a surface having hyperpolarized material disposed thereon and/or therein. The apparatus further includes means for directing a fluid (e.g., liquid or gas) into contact with the surface. The apparatus also includes means for transferring hyperpolarization from the surface to the fluid.

In accordance with a further aspect, the surface may include a plurality of spherical objects, or objects of any other suitable shape. The surface may include material containing nuclei selected from the group including $^{13}C$, $^{15}N$, $^{1}H$, $^{31}P$, $^{19}F$, $^{29}Si$ $^{2}H$ and combinations thereof, among others. The fluid may be a liquid, such as those commonly used as NMR solvents such as water, saline, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof, among others. In accordance with a further aspect, the fluid may additionally or alternatively include a gas, such as one commonly used in inhalation therapy applications including air, nitrogen, carbon dioxide, xenon, $^{3}He$, and combinations thereof, among others.

In further accordance with the invention, a method of producing a hyperpolarized material is provided. The method includes providing a solvent, hyperpolarizing the solvent, and transferring hyperpolarization from the solvent to a target material.

In accordance with a further aspect, the solvent may be mixed with a target material to create a mixture selected from the group including (i) a solution, (ii) a suspension, (iii) an emulsion, (iv) a colloid and (v) a composite material, among others. If desired, the method may further include hyperpolarizing the target material. The target material may be hyperpolarized, for example, through mixing. For example, the target material may be dissolved in the solvent. By way of further example, hyperpolarization may be transferred to the target material by way of electromagnetic coupling. The electromagnetic coupling may be provided, for example, by electromagnetic pulse sequences and used to transfer hyperpolarization from the hyperpolarized solvent to the target.

In accordance with a further aspect, the solvent and target material may be hyperpolarized after they are mixed. If desired, the solvent and/or target material may each be composed of a plurality of component materials that are mixed together. These component materials may be hyperpolarized prior to mixture, during mixture or after mixture.

In accordance with still a further aspect, the solvent may include a liquid suitable for in vitro NMR analysis. For example, the solvent may include a material commonly used as solvents in NMR studies such as water, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof. For in vivo MRI purposes, the liquid is preferably a material commonly used for injection of in vivo solutions and/or suspensions as described herein.

In accordance with yet a further aspect, the method may further include performing an analysis of a region proximate the target material and/or the target material. For example, the analysis may include forming magnetic resonance images of a region of interest such as of a patient. By way of further example, the analysis may include analyzing NMR spectra of an in vitro or in vivo sample or target. The invention also provides a system for producing a hyperpolarized material. The system includes means for providing a solvent, means for hyperpolarizing the solvent, and means for transferring hyperpolarization from the solvent to a target material.

In further accordance with the invention, a method of hyperpolarizing a solvent is provided, as well as a hyperpolarized solvent made in accordance with the method. In accordance with the method, the molecules of the solvent are hyperpolarized by way of a technique selected from the group including (i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the solvent by exposing them to hyperpolarized nuclei of a previously hyperpolarized gas, and combinations thereof.

In accordance with a further aspect, the solvent may include a liquid suitable for in vitro NMR analysis. By way of further example, the solvent may include a physiologically tolerable liquid suitable for use in in vivo MRI studies. For example, the solvent may include a material commonly used as a solvent in NMR studies such as water, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof.

In accordance with still a further aspect, the method may further include arranging the solvent into a high surface area configuration prior to being hyperpolarized. For example, the solvent may be arranged into a high surface area configuration by distributing it onto a high surface area substrate prior to being hyperpolarized. Preferably, the method also includes cleaning the surface of the high surface area substrate of magnetic impurities, such as but not limited to oxygen groups, iron oxides, unpaired electron groups, and the like. In accordance with another aspect, the high surface area substrate is also preferably magnetically inert. By way of example, the high surface area substrate is preferably selected from the group including an aerogel material, silicon beads, fumed silica, carbon nanostructures, silicon nanofibers, exfoliated carbon and combinations thereof, among others.

The method may further include arranging the solvent into a high surface area configuration without use of a substrate. For example, the solvent may be powderized using well understood methods such as spray freezing into liquid (SFL) or spray condensation (SC) techniques.

In accordance with yet a further aspect, the method further includes cooling the solvent prior to hyperpolarizing the solvent. In accordance with one embodiment, the solvent is cooled to a temperature below about 100K prior to hyperpolarizing the solvent. More preferably, the method includes cooling the solvent to a temperature below about 80K, 60K, 40K, 20K, 10K, 5K, or even 1K prior to hyperpolarizing the solvent.

In accordance with another aspect, the method may include exposing the solvent to a magnetic field to facilitate hyperpolarization of the solvent. In accordance with one embodiment, the strength of the magnetic field is greater than about 10 mT. More preferably, the magnetic field has a strength greater than about 0.5 T, 1.0 T, 1.5 T, 2.0 T, 3.0 T, 5.0 T, 7.0 T 10.0 T, 15.0 T, 20.0 T or even 25.0 T. In accordance with yet a further aspect, the method also preferably includes exposing the solvent to helium to facilitate hyperpolarization of the solvent. Even more preferably, the helium includes $^3$He. In accordance with one embodiment, the solvent is exposed to a sufficient quantity of $^3$He to cause at least a monolayer of $^3$He to form on the solvent.

In accordance with a further aspect, the solvent is maintained at a cooled temperature in a magnetic field for a time sufficient to permit relaxation of a substantial portion of the solvent into a state of hyperpolarization. For example, the time sufficient to permit relaxation may vary between several minutes to several hours or even several days, as appropriate, in any time increment.

In accordance with yet another aspect, the method further includes exposing the solvent to $^4$He to displace the $^3$He from the solvent. If desired, the method may also include increasing the temperature of the hyperpolarized solvent. Preferably, the temperature of the hyperpolarized solvent is increased in the presence of a magnetic field having a strength greater than about 1.0 Gauss. Even more preferably, the temperature of the hyperpolarized solvent is increased in the presence of a magnetic field having a strength greater than or equal to about 1.0, 1.5, 3.0, 7.0 Tesla or about 10.0 Tesla. The solvent is preferably increased in temperature within a time sufficient to avoid substantial loss of hyperpolarization. If desired, the temperature of the solvent may be increased to room temperature. If desired, the hyperpolarized solvent may be eluted from the high surface area substrate.

In accordance with still a further aspect the method may include arranging the solvent into a high surface area configuration by converting the solvent into a finely divided form. For example, the solvent may be converted into a powder. The solvent may be converted into a powder, for example, by atomizing and freezing the solvent. If desired, the solvent may be maintained at a low temperature and in a magnetic field for an extended period of time. For example, the extended period of time may be between about one tenth of a second and about one week.

In accordance with still a further aspect, the method may further include transporting the hyperpolarized solvent in a container from a first location to a second location. In accordance with still another aspect, hyperpolarization may be transferred from the hyperpolarized solvent to a sample or other material to be analyzed. The hyperpolarized solvent may be mixed with additional unpolarized solvent containing an analyte to form a solvent mixture before, during or after transport. The resultant mixture may then be delivered to a region of interest to be analyzed. For example, magnetic resonance images may be generated of the region of interest. By way of further example, NMR spectra of the analyte or the metabolic products of the analyte may be measured.

By way of further example, a system for hyperpolarizing various solutions is also provided. In a first system, a solvent is polarized in the manner described above, and an analyte of choice is then dissolved in it. In a second system, the analyte is first dissolved in unpolarized solvent, the resulting solution is then configured as a high surface area arrangement and then hyperpolarized. The high surface area can be achieved either by plating the solution out onto a suitable substrate or by powderizing the solution in the manner described herein.

The system includes means for manufacturing hyperpolarized solutions. As described above, this may include hyperpolarizing a solvent and then dissolving an analyte in it. The method of hyperpolarizing the solvent may include using a technique selected from the group including (i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the solvent by exposing them to hyperpolarized nuclei of a previously hyperpolarized gas, and combinations thereof. Preferably, hyperpolarization is also transferred from the solvent to the analyte added to the solvent. Preferably, the system also includes means for transporting the hyperpolarized solution from a first location to a second location.

By way of further example, the method may include first mixing an analyte with a desired solvent and then hyperpolarizing the resultant solution. The method of hyperpolarizing the solution may include using a technique selected from the group including i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the solvent by exposing them to hyperpolarized nuclei of a previously hyperpolarized gas, and combinations thereof.

Preferably, the system also includes means for transporting the hyperpolarized solution from a first location to a second location.

In still further accordance with the invention, a method of making a hyperpolarized suspension is provided as well as the hyperpolarized suspension itself. The method includes providing a hyperpolarized material and dispersing the hyperpolarized material in a medium to create a hyperpolarized suspension. By way of further example, a hyperpolarized suspension may be provided by hyperpolarizing a medium, dispersing a material in the medium and creating a hyperpolarized suspension. This may include transferring hyperpolarization to the material added to the medium. Moreover, a hyperpolarized suspension may be made by making a suspension from non-hyperpolarized components, and hyperpolarizing the suspension after it is made. Also, a suspension may be provided that is composed of more than two components, wherein one or more of the components of the suspension are hyperpolarized prior to mixing them.

In accordance with a further aspect, the hyperpolarized component or components of the suspension or the suspension itself may be hyperpolarized using a technique selected from the group including i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the component(s) by exposing them to hyperpolarized nuclei of a previously hyperpolarized gas, and combinations thereof. In accordance with yet another aspect, the hyperpolarized component(s) may have a diameter of less than about one thousand microns. More preferably, the hyperpolarized component(s) has a diameter of less than about one hundred microns. Even more preferably, the hyperpolarized component(s) has a diameter of less than about ten microns, five microns or one micron. Preferably, the medium that the hyperpolarized material is dispersed in to form a hyperpolarized suspension is a physiologically tolerable medium. In accordance with another embodiment, the hyperpolarized material is itself a physiologically tolerable material.

In accordance with yet another aspect, the method may further include dispersing the material in the presence of a magnetic field. The magnetic field may have a field strength in excess of 1.0 Gauss. In accordance with still a further aspect, the medium may be selected from the group including (i) a solid, (ii) a liquid and (iii) a gas. For example, the medium may be air. Accordingly, if desired, the method may further include introducing the hyperpolarized suspension into the region of interest, such as the respiratory tract of a patient.

In accordance with still a further aspect, a system for making a hyperpolarized suspension is provided, including means for providing a hyperpolarized material, and means for dispersing the hyperpolarized material in a medium to create a hyperpolarized suspension. Means may also be provided to hyperpolarize a medium and for dispersing a material in the medium to create a hyperpolarized suspension. Moreover, means may be provided for hyperpolarizing the suspension after it is made. Also, means may be provided for making a hyperpolarized suspension that is composed of more than two components, wherein one or more of the components of the suspension are hyperpolarized prior to mixing them by the means. Preferably, the system further includes means for transporting the hyperpolarized suspension from a first location to a second location. It will be understood that the dispersing may occur prior to, during or after transport.

In further accordance with the invention, a method of making a hyperpolarized emulsion is provided, as well as the hyperpolarized emulsion itself. The method includes providing a hyperpolarized material, and mixing the hyperpolarized material with a medium to create a hyperpolarized emulsion. This may include transferring hyperpolarization to the medium from the hyperpolarized material. The method may alternatively include hyperpolarizing a medium and mixing a material into the medium to create a hyperpolarized emulsion. Moreover, a hyperpolarized emulsion may be made by making an emulsion from non-hyperpolarized components, and hyperpolarizing the emulsion after it is made. Also, an emulsion may be provided that is composed of more than two components, wherein one or more of the components of the emulsion are hyperpolarized prior to mixing them.

In accordance with a further aspect, the hyperpolarized material or other component of the emulsion or the emulsion itself may be hyperpolarized using a technique selected from the group including i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the emulsion or component thereof by exposing them to hyperpolarized nuclei of a previously hyperpolarized gas, and combinations thereof. Preferably, the medium that the hyperpolarized material is mixed with to form the hyperpolarized emulsion is a physiologically tolerable medium. In accordance with another embodiment, the hyperpolarized material is itself a physiologically tolerable material.

In accordance with a further aspect, the mixing step may take place in the presence of a magnetic field. Preferably, the mixing step takes place in a magnetic field having a strength of at least about 1.0 Gauss. Moreover, the mixing step may take place at a temperature at which the hyperpolarized material and medium are both in a liquid form. However, if desired, the either hyperpolarized material and medium may be in a solid, liquid or gaseous form when they are mixed.

In accordance with yet a further aspect, a system for making a hyperpolarized emulsion is provided. The system includes means for providing a hyperpolarized material, and means for mixing the hyperpolarized material with a medium to create a hyperpolarized emulsion. This may include means for transferring hyperpolarization to the medium from the hyperpolarized material. Means may also be provided to hyperpolarize a medium and for mixing a material with the medium to create a hyperpolarized emulsion. Moreover, means may be provided for hyperpolarizing the emulsion after it is made. Also, means may be provided for making a hyperpolarized emulsion that is composed of more than two components, wherein one or more of the components of the emulsion are hyperpolarized prior to mixing them by the means. If desired, the system may further include means for transporting the hyperpolarized emulsion from a first location to a second location. It will be understood that the mixing may occur prior to, during or after transport.

In further accordance with the invention, a method of making a hyperpolarized colloid is provided as well as the hyperpolarized colloid itself. The method includes providing a hyperpolarized material, and mixing the hyperpolarized material with a medium to create a hyperpolarized colloid. This may include transferring hyperpolarization to the medium from the hyperpolarized material. The method may alternatively include hyperpolarizing a medium and mixing a material into the medium to create a hyperpolarized colloid. Moreover, a hyperpolarized colloid may be made by making a colloid from non-hyperpolarized components, and hyperpolarizing the colloid after it is made. Also, a colloid may be provided that is composed of more than two components, wherein one or more of the components of the colloid are hyperpolarized prior to mixing them.

In accordance with a further aspect, the hyperpolarized material or other component of the colloid or the colloid itself may be hyperpolarized using a technique selected from the group including i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the colloid or component thereof by exposing them to hyperpolarized nuclei of a previously hyperpolarized gas, and combinations thereof. Preferably, the medium that the hyperpolarized material is mixed with to form the hyperpolarized colloid is a physiologically tolerable medium. In accordance with another embodiment, the hyperpolarized material is itself a physiologically tolerable material.

In accordance with a further aspect, the mixing step may take place in the presence of a magnetic field, such as one having a strength of at least about 1.0 Gauss. Moreover, the mixing step may take place at a temperature at which the hyperpolarized material and medium are both in a liquid form. However, if desired, the either hyperpolarized material and medium may be in a solid, liquid or gaseous form when they are mixed.

In accordance with yet a further aspect, a system for making a hyperpolarized colloid is provided. The system includes means for providing a hyperpolarized material, and means for mixing the hyperpolarized material with a medium to create a hyperpolarized colloid. This may include transferring hyperpolarization to the medium from the hyperpolarized material. Means may also be provided to hyperpolarize a medium and for mixing a material with the medium to create a hyperpolarized colloid. Moreover, means may be provided for hyperpolarizing the colloid after it is made. Also, means may be provided for making a hyperpolarized colloid that is composed of more than two components, wherein one or more of the components of the colloid are hyperpolarized prior to mixing them by the means. If desired, the system may further include means for transporting the hyperpolarized colloid from a first location to a second location. It will be understood that the mixing may occur prior to, during or after transport.

In further accordance with the invention, a method of making a hyperpolarized composite material is provided, as well as the hyperpolarized composite material made in accordance with the method. The method includes providing a hyperpolarized material, and mixing the hyperpolarized material with a second material, such as a medium, to create a hyperpolarized composite material. This may include transferring hyperpolarization to the second material from the hyperpolarized material. The method may alternatively include hyperpolarizing a medium and mixing a material into the medium to create a hyperpolarized composite material. Moreover, a hyperpolarized composite material may be made by making a composite material from non-hyperpolarized components, and hyperpolarizing the composite material after it is made. Also, a composite material may be provided that is composed of more than two components, wherein one or more of the components of the composite material are hyperpolarized prior to mixing them.

In accordance with a further aspect, the hyperpolarized material, component of the composite material or composite material itself may be hyperpolarized using a technique selected from the group including (i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to a component of the composite by exposing it to hyperpolarized nuclei of a previously hyperpolarized gas, and combinations thereof. Preferably, the medium that that the hyperpolarized material is mixed with to form the hyperpolarized composite material is a physiologically tolerable medium. In accordance with another embodiment, the hyperpolarized material is itself a physiologically tolerable material.

By way of further example, the composite material may include an encapsulated material such as one having a polymeric shell and may include a substance such as TentaGel. By way of further example, the composite material may also include a liposome containing or otherwise including hyperpolarized material.

In accordance with still a further aspect, the mixing step may take place in the presence of a magnetic field. Preferably, the magnetic field has a strength of at least about 1.0 Gauss. The hyperpolarized material may be selected from the group including (i) a solid material, (ii) a liquid material, (iii) a gaseous material and combinations thereof. The medium may be selected from the group including water and saline, among others. If desired, one could also select as the dispersing medium gases commonly used in inhalation therapy such as air, nitrogen, carbon dioxide, xenon, $^3$He and the like.

In accordance with yet a further aspect, a system for making a hyperpolarized composite material is provided. The system includes means for providing a hyperpolarized material, and means for mixing the hyperpolarized material with a medium to create a hyperpolarized composite material. Means may also be provided to hyperpolarize a medium and for mixing a material with the medium to create a hyperpolarized composite material. Moreover, means may be provided for hyperpolarizing the composite material after it is made. Also, means may be provided for making a hyperpolarized composite material that is composed of more than two components, wherein one or more of the components of the composite material are hyperpolarized prior to mixing them by the means. If desired, the system may further include means for transporting the hyperpolarized composite material from a first location to a second location. It will be understood that the mixing may occur prior to, during or after transport. If desired, the hyperpolarized composite material or components thereof may be selected from the group including (i) a solid material, (ii) a liquid material, (iii) a gaseous material and combinations thereof, for example.

In further accordance with the invention, a beneficial agent is provided. In accordance with one embodiment of the invention, the beneficial agent includes a hyperpolarized core material surrounded by a porous encapsulating medium.

In accordance with a further aspect, the porosity of the encapsulating medium may substantially permit passage of gas through the encapsulating medium to the core material. For example, the porosity of the encapsulating medium may substantially permit passage of helium through the encapsulating medium, but may also substantially prohibit passage of gas molecules through the encapsulating medium larger than helium.

In accordance with still a further aspect, the hyperpolarized core material may have a relatively long spin-lattice relaxation time. For example, the hyperpolarized core material may include material containing nuclei such as $^{13}$C, $^{15}$N, $^1$H, $^2$H, $^{31}$P, $^{19}$F, $^{29}$Si and combinations thereof, among others.

In accordance with still another aspect, the encapsulating medium may include polymeric material. The polymeric material may include a material selected from the group including polytetrafluoroethylene, poly(lactic-co-glycolic acid), polyanhydrides, polyorthoesters, polyvinylalchols, and combinations thereof. Preferably, the encapsulating material is adapted and configured to substantially maintain its structural integrity at temperatures below 100K, 10K and 1K, if desired. By way of further example, the encapsulating material may also include hyperpolarized material.

In accordance with another embodiment, the encapsulating medium includes a biologically derived medium such as a liposome. The liposome may be adapted and configured to include hyperpolarized material therein or thereon. The material of the liposome itself may also be hyperpolarized using any suitable technique disclosed herein. For example, the liposome may be exposed to a hyperpolarized liquid (e.g., solvent, solution, suspension, emulsion, colloid, etc.) or gas. The liposome may absorb hyperpolarized fluid (e.g., liquid) and then be directed to a region of interest. Alternatively, the large dipolar field generated by any of the above hyperpolarized materials may be used to transfer polarization through the liposome barrier. The hyperpolarized material that is in, on, or that composes, the liposome can be used, for example, to pinpoint the location of a tumor or other anatomy of interest in MR imaging, or may be used in NMR studies, as appropriate.

In accordance with one embodiment, the liposome is provided with hyperpolarized pyruvate. The liposome can be used to target delivery of the hyperpolarized pyruvate to a desired location in a region of interest such as a portion of a patient to permit detection of the presence of metabolic processes that consume the pyruvate by using NMR/MRI techniques.

In accordance with a further aspect, the hyperpolarized core material may include material that is solid at standard conditions. For example, the hyperpolarized core material may include material that is liquid, gaseous or solid at standard conditions. If desired, the beneficial agent may be provided in the form of a capsule having an average diameter between about 0.001 microns and about 100 microns that may be used for in vivo or in vitro studies. Preferably, the beneficial agent is provided in the form of a capsule having an average diameter between about 0.001 microns and about 10 microns.

In accordance with a further aspect, the beneficial agent may include a functional element disposed proximate the encapsulating medium, the functional element being adapted and configured to facilitate a beneficial result in use. The core material may be selected from the group including hexafluorobenzene, perfluorocarbons, and the like.

The invention also provides a beneficial agent including a hyperpolarized core material surrounded by an encapsulating medium, wherein the hyperpolarized core material includes material selected from the group including (i) liquid material, (ii) solid material, (iii) gaseous material interspersed with a solid material, (iv) gaseous material interspersed with a liquid material, and combinations thereof.

In accordance with a further aspect, the encapsulating medium may be porous. The porosity of the encapsulating medium may substantially permit passage of gas through the encapsulating medium to the core material. For example, the porosity of the encapsulating medium may substantially permits passage of helium through the encapsulating medium, and if desired, may substantially prohibit passage of gas molecules through the encapsulating medium larger than helium.

In accordance with still a further aspect, the hyperpolarized core material may have a relatively long spin-lattice relaxation time. For example, the hyperpolarized core material may include material selected from the material containing nuclei such as $^{13}$C, $^{15}$N, $^{1}$H, $^{2}$H, $^{31}$P, $^{19}$F, $^{29}$Si and combinations thereof. If desired, the encapsulating medium may include polymeric material. The polymeric material may include a material selected from the group including polytetrafluoroethylene, poly(lactic-co-glycolic acid), polyanhydrides, polyorthoesters, polyvinylalchols, and combinations thereof. Preferably, the encapsulating medium is adapted and configured to substantially maintain its structural integrity at temperatures below 100K. More preferably, the encapsulating medium is adapted and configured to substantially maintain its structural integrity at temperatures below 10K. Even more preferably, the encapsulating medium is adapted and configured to substantially maintain its structural integrity at temperatures below 1K. If desired, the encapsulating material may include hyperpolarized material.

In accordance with yet a further aspect, the beneficial agent may be composed of materials that are acceptable for use in vivo. If desired, the beneficial agent may be provided in the form of a capsule having an average diameter between about 0.001 microns and about 100 microns. Even more preferably, the beneficial agent may be provided in the form of a capsule having an average diameter between about 0.001 microns and about 10 microns. As with other embodiments described herein, the beneficial agent may further include a functional element disposed proximate the encapsulating medium that is adapted and configured to facilitate a beneficial result in use. For example, the core material may be selected from the group including hexafluorobenzene, perfluorocarbons, and the like.

In further accordance with the invention, a kit for providing hyperpolarized material is provided. The kit includes at least one encapsulated material. The encapsulated material includes a core material, which in turn includes a material having a relatively long spin-lattice relaxation time. The encapsulated material further includes an encapsulating medium surrounding the core material. The kit also includes instructions for facilitating hyperpolarization of the encapsulated material.

In accordance with a further aspect, the encapsulating medium may be porous as described herein. The core material may include material selected from the group including those materials containing nuclei such as $^{13}$C, $^{15}$N, $^{1}$H, $^{2}$H, $^{31}$P, $^{19}$F, $^{29}$Si and combinations thereof. The encapsulating medium may also include polymeric material as described herein. For example, the polymeric material may include a material selected from the group including polytetrafluoroethylene, poly(lactic-co-glycolic acid), polyanhydrides, polyorthoesters, polyvinylalchols, and combinations thereof. In accordance with a further aspect, the encapsulating medium may be adapted and configured to substantially maintain its structural integrity at depressed temperatures such as those below 100K, 10K and 1K. Moreover, the encapsulating medium may be adapted and configured to substantially maintain its structural integrity in the presence of a magnetic field of varying strengths, such as those in excess of 10 mT, 1 T and 10 T among others. In accordance with still a further aspect, the encapsulating material of the kit may include material having a relatively long spin-lattice relaxation time. The core material may include material that is solid, liquid and/or gaseous at standard conditions.

In accordance with yet a further aspect, the instructions for the kit may describe how to facilitate hyperpolarization of the encapsulated material using a quantum relaxation switch. By way of further example, the instructions of the kit may describe how to facilitate hyperpolarization of the encapsulated material by transferring hyperpolarization from a hyperpolarization carrier to the core material.

In accordance with still a further aspect, the core material may be hyperpolarized using a technique selected from the group including (i) dynamic nuclear polarization, (ii) the Nuclear Overhauser effect, (ii) parahydrogen induced polarization, (iii) hyperpolarization using a brute force environment, most preferably in conjunction with a quantum relaxation switch (iv) transferring hyperpolarization to molecules of the core material by exposing them to hyperpolarized nuclei of a previously hyperpolarized gas, and combinations thereof.

In further accordance with the invention, a method of preparing and providing hyperpolarized encapsulated material is provided. In accordance with a first aspect, the method includes providing an encapsulated material, providing a hyperpolarization carrier or hyperpolarization facilitator (e.g., $^3$He), exposing the encapsulated material to the hyperpolarization carrier or facilitator and transferring hyperpolarization from the hyperpolarization carrier to the encapsulated material or using the hyperpolarization facilitator to facilitate hyperpolarization of the material.

In accordance with a further aspect, the hyperpolarization carrier may be hyperpolarized using a technique selected from the group including (i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the solvent by exposing them to hyperpolarized nuclei of a previously hyperpolarized gas, and combinations thereof.

In accordance with still a further aspect, the encapsulated material may have a porous surface portion to permit passage of the hyperpolarization carrier or hyperpolarization facilitator therethrough as described herein. The porous surface portion preferably permits passage of the hyperpolarization carrier or hyperpolarization facilitator therethrough into a core portion of the encapsulated material. The core portion may include material that is solid, liquid and/or gaseous at standard conditions. The porous surface portion of the capsule may include polymeric material, such as polytetrafluoroethylene, poly(lactic-co-glycolic acid), polyanhydrides, polyorthoesters, polyvinylalchols, and combinations thereof.

In accordance with another aspect, the hyperpolarization carrier may pass through the surface portion to the core portion. For example, the hyperpolarization carrier may include gaseous hyperpolarized xenon. In accordance with still a further aspect, the core portion may include material selected from the group including $^{13}$C, $^{15}$N, $^1$H, $^{31}$P, $^{19}$F, $^{29}$Si and combinations thereof.

In accordance with a further aspect, the method may further include cooling the encapsulated material. Preferably, the encapsulated material is cooled to a temperature below about 100K, 10K or 1K. The method may additionally or alternatively include exposing the encapsulated material to a magnetic field, such as a magnetic field having a maximum strength in excess of 10 mT, 1 T, or 10 T, for example.

The invention also provides a method of preparing and providing hyperpolarized encapsulated material using a hyperpolarization facilitator that acts as a quantum relaxation switch. The method includes providing an encapsulated material, and facilitating the hyperpolarization of the encapsulated material using a quantum relaxation switch.

In accordance with a further aspect, the encapsulated material may be exposed to $^3$He. Preferably, the encapsulated material has a porous surface portion to permit passage of the $^3$He therethrough. Even more preferably, the porous surface portion permits passage of a gas therethrough into a core portion of the encapsulated material. The core portion may include a material that is solid, liquid and/or gaseous at standard conditions. In accordance with another aspect, the porous surface portion of the capsule may include polymeric material, such as polytetrafluoroethylene, poly(lactic-co-glycolic acid), polyanhydrides, polyorthoesters, polyvinylalchols, and combinations thereof, among others. In accordance with one embodiment, the porosity of the encapsulating medium may substantially permit passage of helium through the encapsulating medium and may substantially prohibit passage of molecules through the encapsulating medium larger than helium. Preferably, the core portion includes material containing nuclei selected from the group including $^{13}$C, $^{15}$N, $^1$H, $^2$H, $^{31}$P, $^{19}$F, $^{29}$Si and combinations thereof, among others.

In accordance with still a further aspect, the encapsulated material may be cooled and/or maintained in a magnetic field to facilitate hyperpolarization of the encapsulated material. For example, the encapsulated material may be cooled to a temperature below about 100K, 10K or 1K, among others. By way of further example, the magnetic field may have a maximum strength in excess of about 10 mT, 1 T or 10 T, among others. Preferably, the core material is maintained at a cooled temperature in a magnetic field for a time sufficient time to permit relaxation of at least a portion of the core material into a state of hyperpolarization.

In accordance with a further aspect, the core material may be exposed to $^4$He to displace the $^3$He from the core material, thus preserving the hyperpolarization of the core material, but removing the $^3$He. In accordance with one embodiment, the hyperpolarized encapsulated material may be maintained at a low temperature and/or in a magnetic field for an extended period of time. Maintaining the hyperpolarized material in such a manner facilitates storage and/or transport of the material, and minimizes loss of hyperpolarization from the material. The extended period of time can be any suitable time period, between about one tenth of a second and about one week, for example, and in any suitable time increment. If transporting the material for an end use at another location, the hyperpolarized encapsulated material may be transported in a suitable container from a first location to a second location, preferably at a low temperature and in the presence of a magnetic field.

If desired, the encapsulated material may be maintained at a low temperature and in a magnetic field for an extended period of time, such as between about one tenth of a second and about one week. The encapsulated hyperpolarized material may be transported in a container from a first location to a second location. Prior to using the encapsulated hyperpolarized material, the temperature of the encapsulated material may first be increased in a manner such that substantial loss of hyperpolarization is avoided. The encapsulated hyperpolarized material may then be introduced into a region of interest to be analyzed. For example, magnetic resonance images of the region of interest may be generated. By way of further example, NMR spectra of an in vitro or in vivo target or sample may be analyzed.

In accordance with still another aspect, the hyperpolarized encapsulated material may be increased in temperature for use. Preferably, the temperature of the encapsulated material is increased in a manner that minimizes a substantial loss of the material's hyperpolarization. The encapsulated hyperpolarized material may then be introduced into a region of interest to be analyzed. If desired, magnetic resonance images may then be generated of the region of interest. By way of further example, NMR spectra of an in vitro or in vivo sample or target may be analyzed using the hyperpolarized material.

In still further accordance with the invention, a method of obtaining a magnetic resonance image of a region of interest such as of a patient is provided. The method includes introducing a hyperpolarized encapsulated material into a region of interest such as of a patient, transmitting a pulse or pulses of electromagnetic energy into the region of interest to excite the hyperpolarized encapsulated material, and creating a magnetic resonance image of the region of interest using a signal received from the hyperpolarized encapsulated material.

The invention also provides a method of performing NMR spectroscopy. The method includes introducing a hyperpolarized encapsulated material into a region of interest, transmitting a pulse or pulses of electromagnetic energy into the region of interest to excite the hyperpolarized encapsulated material, and receiving NMR spectra from the region of interest.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 6 is a schematic view of a sixth system made in accordance with the present invention.

FIGS. 7(A)-7(F) are schematic views of a method and process for manufacturing a beneficial agent made in accordance with the present invention.

DETAILED DESCRIPTION OF THE PREFERRED EMBODIMENT

Reference will now be made in detail to the present preferred embodiments of the invention, examples of which are illustrated in the accompanying drawings. The method and corresponding steps of the invention will be described in conjunction with the detailed description of the system.

The devices, methods and compositions presented herein may be used for enhancing the efficacy of MRI and/or NMR. Certain embodiments of the present invention are particularly suited for providing hyperpolarized material to an end user at a location that is remote from the location where the material was initially hyperpolarized. Moreover, other embodiments of the invention provide an encapsulated hyperpolarized material that facilitates analysis of samples, materials and patients, as desired.

In accordance with a first embodiment of the invention, a method of producing a hyperpolarized material is provided. The method includes providing a first material, increasing the nuclear hyperpolarization of the first material until the first material becomes hyperpolarized, and transferring the hyperpolarization from the first material to a second material.

Figure 1:
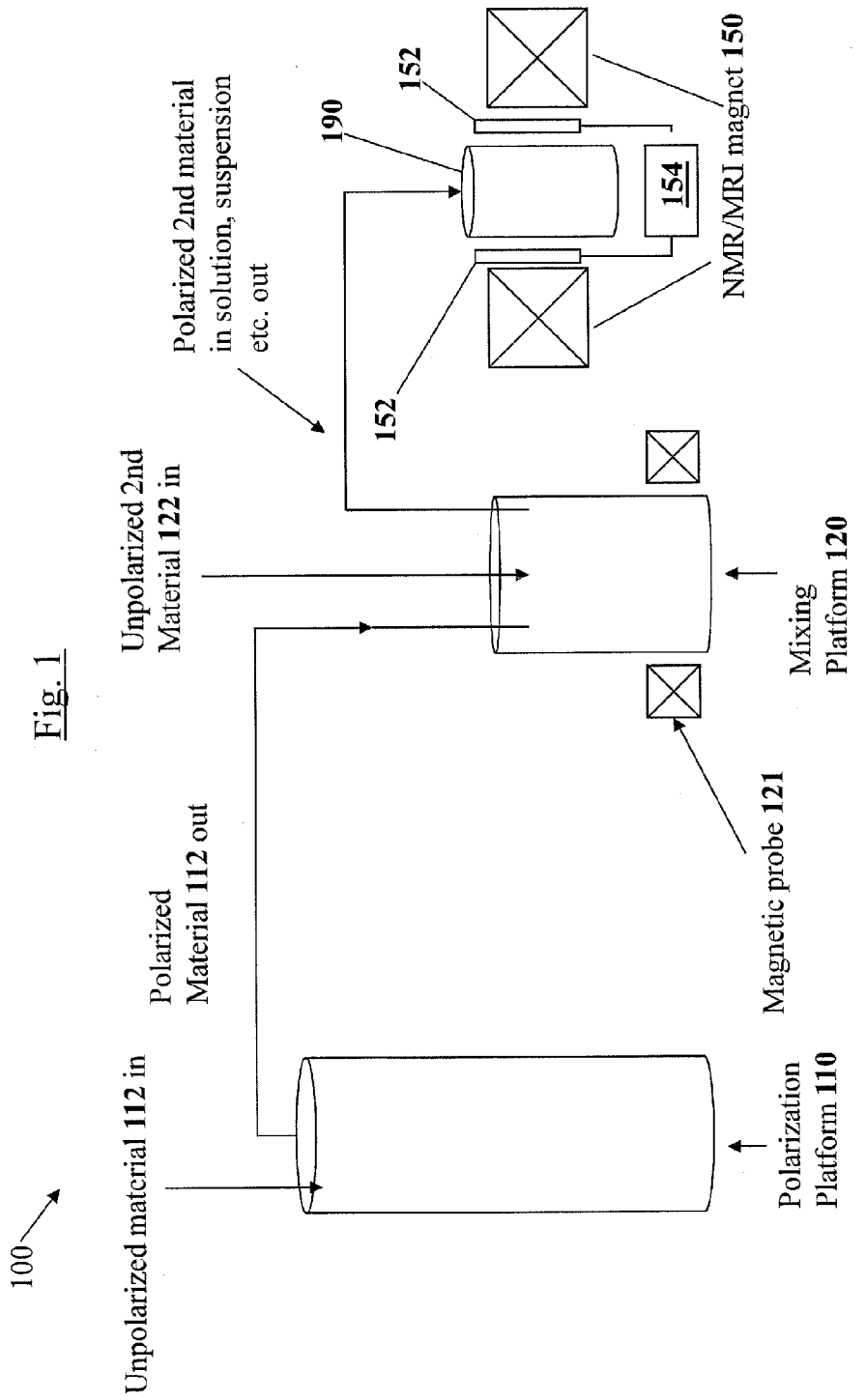
FIG. 1 is a schematic view of a first system made in accordance with the present invention.

For purpose of explanation and illustration, and not limitation, a schematic view depicting method steps of an exemplary method and system carried out in accordance with the invention is shown in FIG. 1 and is designated generally by reference character 100. Other embodiments of a method and/or system in accordance with the invention, or aspects thereof, are provided in FIGS. 2-7, as will be described.

Thus, as illustrated in FIG. 1, for example, a first material 112 is provided that is directed into a hyperpolarization platform 110. The nuclear hyperpolarization of the first material 112 is increased until the first material 112 becomes hyperpolarized.

Nuclear hyperpolarization can be written as $(N\uparrow - N\downarrow)/(N\uparrow + N\downarrow)$, where $N\uparrow$ represents the number of nuclei in the material with their nuclear magnetic moment aligned parallel to the direction of an external magnetic field, and $N\downarrow$ represents the number of nuclei in the material with their nuclear magnetic moment aligned antiparallel to the direction of an external magnetic field. As used herein, the term hyperpolarization is intended to refer to an increase in the spin ordering of an ensemble or set of ensembles of nuclear spins such that the MR signal from the ensemble(s) is enhanced over and above what it would otherwise be under standard operating conditions. This increase may be accomplished artificially. Under standard NMR/MRI operating conditions (T=300 K, B=1-10 Tesla) $N\uparrow \sim N\downarrow$ and the overall polarization of even protons is still quite low, on the order of a few ppm. Hyperpolarization refers to the act of artificially aligning a high percentage of the nuclear spins in a given direction; typically, along the direction of the applied magnetic field. The signal to noise ratio in an NMR/MRI is a direct function of the polarization P:

$$S/N \sim (Q f_0 t_{exp}/T_1)^{1/2} c(xyz) P$$

Hence by hyperpolarizing spins to a value of (for example) 10%, the signal to noise ratio can be increased by a factor of 10,000 or more depending on the target nuclei.

A variety of techniques can be used by hyperpolarization platform 110 to hyperpolarize the first material 112. It will be understood in the context of the subject disclosure that these techniques as described herein can be used to hyperpolarize any of the useful hyperpolarized compositions described herein (e.g., solvents, solutions, suspensions, emulsions, colloids, composite materials, and the like) or one or more components thereof.

As a first example, dynamic nuclear polarization ("DNP") may be used to hyperpolarize the first material 112 (or other material). DNP generally involves transfer of polarization from electron spins to nearby nuclear spins; typically, although not exclusively, via saturation of the electron resonance line using microwave irradiation. An example of DNP in the patent literature includes U.S. Pat. No. 6,008,644 which is incorporated by reference herein in its entirety. In the context of certain of the embodiments of the present invention, DNP can be used to hyperpolarize the solvent and/or physiologically tolerable fluid. The hyperpolarization of the solvent or fluid is then later transferred to the analyte of interest.

As a second example, the Nuclear Overhauser effect can be used to hyperpolarize the first material 112 (or other material). The Nuclear Overhauser effect generally involves transfer of nuclear polarization from one set of nuclear to spins to another set of nearby nuclear spins; typically, though not exclusively, by saturation of the first set of spins nuclear resonance line. Examples of the Nuclear Overhauser effect in the literature are described in Schlichter, Principles of Magnetic Resonance, 2nd ed. Springer Velas, Berlin, 1978, which is incorporated by reference herein in its entirety.

In the context of certain of the embodiments of the present invention, the Nuclear Overhauser effect can be employed by causing one set of nuclear spins in the solvent and/or physiologically tolerable fluid to have a higher than usual polarization. This excess polarization of the solvent and/or physiologically tolerable fluid may then later transferred to the analyte of interest.

As a third example, parahydrogen induced polarization ("PHIP") can be used to hyperpolarize the first material 112 (or other material). PHIP generally involves transfer of polarization via catalyzed hydrogenation by p-$H_2$, followed by spin-order transfer to the nucleus of interest. Examples of PHIP in the patent literature include, for example, U.S. Pat. No. 6,574,495, which is incorporated by reference herein in its entirety. In the context of certain of the embodiments of the present invention, PHIP can be employed, for example, by using PHIP to hyperpolarize the nuclei of the solvent and/or physiologically tolerable fluid. The nuclear hyperpolarization of the solvent and/or physiologically tolerable fluid may then later be transferred to the analyte of interest.

As a fourth example, brute force hyperpolarization preferably using a quantum relaxation switch (referred to herein as "QRS") can be used to hyperpolarize the first material 112 (or other material). As a term in the art, brute force refers to exposing the material to be hyperpolarized to very low temperature, high magnetic field conditions. Materials in a "brute force" environment will tend to naturally relax to a state of high nuclear polarization. However, without use of additional mechanisms, the time to achieve hyperpolarization is generally too long to be of practical use. By using a hyperpolarization facilitator such as $^3$He, a quantum relaxation switch provided by the $^3$He facilitates relaxation of the material under while in brute force conditions to rapidly induce hyperpolarization in the material. Application of $^4$He is then used to remove the $^3$He from the surface of the first material 112 to enable it to be warmed to room temperature without undue loss of hyperpolarization. An example of QRS in the patent literature includes U.S. Pat. No. 6,651,459 which is incorporated by reference herein in its entirety. In the context of certain of the embodiments of the present invention, QRS can be employed by causing the nuclei in the solvent to relax to a state of high nuclear polarization. The hyperpolarization of the solvent and/or physiologically tolerable fluid can then later be transferred to nuclei in the analyte of interest.

As a fifth example, molecules of the first material 112 or other material may be hyperpolarized by exposing them to hyperpolarized nuclei of a previously hyperpolarized gas. This can be carried out in a variety of ways, such as by immersing the first material in liquefied hyperpolarized $^{129}$Xe, or by allowing gaseous polarized xenon to be bubbled through the material. An example of nuclear hyperpolarization transfer from a gas in the patent literature can be found in U.S. Pat. No. 6,426,058 which is incorporated by reference herein in its entirety. In the context of certain of the embodiments of the present invention, this can be employed by hyperpolarizing the solvent and/or physiologically tolerable fluid. The nuclear hyperpolarization of the solvent and/or physiologically tolerable fluid may then later be transferred to nuclei in the analyte of interest.

As described herein, the "Overhauser effect", is considered to be the transfer of polarization from an electron to a nucleus. As further described herein, the "Nuclear Overhauser Effect" is a similar phenomena, except that the transfer is from one nucleus to another. In each case polarization is transferred from one set of spins (electron-nucleus in the case of the "Overhauser Effect", nuclear-nuclear in the case of the "Nuclear Overhauser Effect"). The techniques may utilize application of radiofrequency ("RF") pulses to the material, or not, depending on whether the two sets of spins (i.e., (i) electron-nucleus or (ii) nucleus-nucleus) are in motion with respect to one another.

Preferably, in accordance with one embodiment of the invention, when performing DNP, the electrons are highly polarized and in close contact with the nuclei of interest to be polarized. This may advantageously be accomplished by employing low temperatures (such as about 1.6 K or below) while in the presence of a magnetic field, such as on the order of 3 Tesla. In DNP, the electron spins are static with respect to the nuclei of interest. As such, the electron resonance line may be saturated using microwave radiation. Moreover, it is also preferable to irradiate the nuclei of interest with microwaves to facilitate the transfer of polarization when performing DNP.

More broadly speaking, by employing the teachings herein, it is possible to transfer hyperpolarization to a first material without a need to resort to applying microwave pulses to facilitate hyperpolarization transfer including even the Nuclear Overhauser effect, although the use of microwaves for this purpose, if desired, is clearly within the scope of the instant disclosure.

Once first material 112 (or other material) has been hyperpolarized it may be used for a variety of purposes. First material 112 may be used to hyperpolarize a second material, discussed in detail below, or may be used for other purposes. First material 112 may be stored in hyperpolarized form for an extended period of time at the location where it was polarized, or may be transported to a second location for storage and/or further use. If desired, first material may be liquefied or frozen for storage and/or transport.

As further depicted in FIG. 1, if desired, hyperpolarization may be transferred from the first material 112 to a second material 122 using the mixing platform 120. A magnet and probe 121 may be optionally included in the mixing platform to allow for application of RF pulses of appropriate frequency and magnitude to facilitate transfer of polarization. Transfer of hyperpolarization may be achieved in a number of ways.

The availability of several techniques to transfer hyperpolarization between unlike nuclear species is well understood in the art and has been discussed in Pietraβ, T.: Optically Polarized $^{129}$Xe in Magnetic Resonance Techniques. Magn. Reson. Rev. 17, 263-337 (2000), the contents of which are incorporated herein by reference in their entirety. These techniques are:

1) Cross polarization
2) The Nuclear Overhauser effect
3) Thermal mixing; and
4) Larmor/Rabi Frequency Cross Coupling The above techniques all refer to methods of transferring polarization between unlike spins. In addition, intimate coupling between like spins in the two materials can be facilitated by ensuring good thermal, chemical and/or dipolar contact between the materials. It will be recognized that the mixing platform may therefore include apparatus to expose the materials or materials to RF pulses of appropriate frequency and magnitude; or, in the case where RF excitation of the materials is not required, the mixing apparatus may include an appropriate mixing system (e.g., a mechanical mixing system) to ensure good thermal, chemical and/or dipolar contact between the two materials to provide intimate contact between the materials to facilitate hyperpolarization transfer.

All of the above techniques may be used to transfer nuclear hyperpolarization from the first material to a second material.

Advantageously, there needs to be good dipolar coupling between the two sets of nuclear spins in the first and second materials.

Cross-Polarization:

In cross polarization, radiofrequency pulses are used to induce mutual spin flips between dissimilar, dipolar coupled, spins where one set of spins is in, or is caused to be in, a higher state of nuclear order. The assumption is that the spins are in static motional relationship (i.e., their mutual tumbling rate is low) to one another and satisfy the condition $\gamma_1 B_S = \gamma S B_I$.

Radiofrequency pulses are then applied to one set of spins to cause saturation of its resonance line. This can be accomplished by use of a spectrometer capable of delivering radiofrequency pulses to the materials of interest. By way of further example, most installed NMR/MRI magnets either already have this capability or could be readily upgraded to have such a capability. This technique may therefore be used to transfer hyperpolarization from a first material to a second material or to create a hyperpolarized (i) solution, (ii) suspension, (iii) emulsion or (iv) composite material as described herein, such as by hyperpolarizing these mixtures after they are made, or by hyperpolarizing one or more constituents of these mixtures before they are made.

Nuclear Overhauser Effect:

In contrast to cross polarization described above, the Nuclear Overhauser Effect proceeds by mutual "flip flop" transitions between dipolar coupled spins. If the physical situation is one in which one set of spins is tumbling rapidly in relation to the other (a situation well described by two liquids mixing together or one liquid flowing past a solid object) then the rapidly varying dipolar field from one set of spins causes transitions in the other and irradiating radiofrequency pulses are not required for hyperpolarization to be transferred between dissimilar nuclei. For applications embodied herein, for example, this effect can be facilitated by ensuring that the hyperpolarized material 112 be thoroughly mixed with the second material 122.

Even if the spins are not tumbling with respect to one another, a rapidly varying dipolar field can be created by saturation of the hyperpolarized nuclei's resonance line. It will be understood that in either case the technique can be used to transfer hyperpolarization from a first material to a second material or to create a hyperpolarized (i) solution, (ii) suspension, (iii) emulsion or (iv) composite material, as embodied herein.

Thermal Mixing:

Thermal mixing usually refers to the act of transferring polarization between dissimilar nuclei by quickly decreasing an external magnetic field such that the Zeeman energy of the separate nuclei for a brief time are overlapping. The main criterion is generally that the Zeeman energy reservoirs $E = \gamma_{I,S} B$ of the dissimilar nuclei I, S be as closely matched as possible.

This technique has the advantage of not requiring application of radiofrequency pulses to achieve hyperpolarization transfer. A disadvantage of ordinary thermal mixing is that it normally requires the materials being mixed to be exposed for a brief time to a very low magnetic field. Since $T_1$ is often a strong function of magnetic field this can lead to a steep loss of polarization in at least one of the materials and degradation of results.

However, in various applications disclosed herein, the first material and second material may be pre arranged to contain identical and dipolar coupled nuclei. For example, $^{13}C$ spins in a material such as a solvent may be dipolar coupled with $^{13}C$ spins in the analyte. In this instance it is not necessary to lower the field to achieve good hyperpolarization transfer.

The spins in the solvent and in the analyte should be in good dipolar coupling with one another for a sufficiently long time to achieve hyperpolarization transfer. In the case of good coupling the time to transfer hyperpolarization can be quite short (e.g., on the order of 1E-4 sec). As such, the systems and methods embodied herein achieves good coupling by assuring good mixture between, for example, the hyperpolarized solvent and the analyte as described above.

Thermal mixing therefore can be used to transfer hyperpolarization from a first material to a second material or to create a hyperpolarized (i) solution, (ii) suspension, (iii) emulsion and/or (iv) composite material, as desired, among others.

Larmor/Rabi Frequency Cross Coupling:

Under conditions where $\gamma_S B_1 = \gamma_1 B_0$, coupling between spins S,I may be accomplished. This technique requires only a single RF excitation but does require that the $B_1$ tipping field be very large if the coupling is carried out in a large field $B_0$.

In each of the situations described above it will be recognized that it is desirable to have the following characteristics in transferring hyperpolarization from a first material to a second material:

1) A high degree of hyperpolarization in the first material. This may be achieved by any of the methods described above. In accordance with a preferred embodiment, this is achieved by employing a brute force ("BF") quantum relaxation switch ("QRS").

2) Good thermal and dipolar contact between the first material and the second material. This can be achieved by causing the first material and second material to be mixed in a manner to achieve good dipolar contact between the nuclear spins in the first material, and, if desired, employing irradiating electromagnetic pulses as needed to ensure good hyperpolarization transfer between the nuclei in the two materials.

Polarization Transfer Between Nuclear Spins in Dissimilar Materials

In the art, all the above techniques are typically used to transfer hyperpolarization between nuclei in a molecular bond. However, hyperpolarization transfer between dissimilar species and in dissimilar physical states has been amply demonstrated. For example, transfer of hyperpolarization between dissimilar solid species has been demonstrated in "Nuclear spin polarization transfer across an organic-semiconductor interface," *Journal of Chemical Physics* Volume 119, Number 19 15 Nov. 2003, Lucas Goehring and Carl A. Michal. This publication is expressly incorporated by reference In this reference an organic material was overlaid on top of a polarizable substrate such as InP. Polarization from the $^{31}P$ nuclei in the InP was transferred to the spins in the organic overlayer via application of radiofrequency pulses, and hyperpolarization transfer in the overlaid layer itself proceeded via spin diffusion.

Similarly, nuclear hyperpolarization can be transferred between spins in a solvent and spins in a solute. For example, in *J. Am. Chem. Soc.* 2001, 123, 1010-1011, which is incorporated by reference herein in its entirety, nuclear polarization in the proton ensemble spread by spin diffusion between the solvent and solute. In this particular instance, application of electromagnetic pulses are not needed as the Zeeman energy levels of the nuclei are identical.

Similarly, polarization transfer between hyperpolarized xenon and dissimilar spins has been demonstrated using thermal mixing in Volume 205, number 2,3 *Chemical Physics Letters,* 9 Apr. 1993 "Cross polarization from laser-polarized solid xenon to $^{13}CO_2$ by low-field thermal mixing" C. R. Bowers, H. W. Long, T. Pietrass, H. C. Gaede and A. Pines. This publication is also incorporated by reference herein in its entirety.

As further embodied herein, thorough mixing may be achieved by passing first material 112 over or through second material 122 in platform 120 to achieve sufficient physical contact to permit hyperpolarization of second material 122. For example, as discussed below with reference to FIG. 2, first material 112 can be provided in the form of solid beads 212 having hyperpolarized material at the surface. Particular examples of suitable beads or materials for making those beads include, for example, silicon microspheres, carbon microspheres, carbon nanotubes, carbon nanofibers, polymer resins such as TentaGel™ (Rapp Polymere GmbH, Ernst-Simon-Str. 9, D 72072 Tübingen, Germany), and the like. TentaGel resins are grafted copolymers consisting of a low crosslinked polystyrene matrix on which polyethylene glycol (PEG or POE) is grafted. As PEG is a "chameleon type" polymer with hydrophobic and hydrophilic properties, the graft copolymer shows modified physio-chemical properties.

It will be recognized that, although alteration of the external field, either of the main NMR/MRI magnet 150 and/or the holding field arising from the holding magnet 360 in the transfer Dewar 300, is not necessarily an optimum route to achieve increased hyperpolarization in the analyte, such a method may also be used for hyperpolarization transfer.

In accordance with a further aspect, at least one of the first material and second material are preferably suitable for in vitro or in vivo NMR analysis. Moreover, at least one of the first material and second material are preferably tolerable liquid suitable for use in in vivo MRI studies. Liquid materials may be used for the first material 112 and/or second material 114, such as water, saline solution, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof. In accordance with a further aspect, the fluid may additionally or alternatively include a gas, such as one selected from the group including air, nitrogen, carbon dioxide, xenon, $^3$He, and combinations thereof, among others. Moreover, solid materials may also be used for one or more of first material 112 and second material 122, such as including $^{13}$C, $^{15}$N, $^1$H, $^2$H, $^{31}$P, $^{19}$F, $^{29}$Si and combinations thereof.

After hyperpolarizing first material 112 or second material 122 (or other material), if desired, it is possible to preserve the hyperpolarization of the material, such as by maintaining the material at a depressed temperature and in a magnetic field, and transporting it to a location where it may be used in analysis. Thus, it is possible to create a hyperpolarized material 112 in a first location, and transport it to a second location where the hyperpolarization may be transferred to second material 122. A suitable container, such as container 205 described in detail below, may be used for such a purpose. Alternatively, if desired the hyperpolarization transfer may take place in the first location, and the second material may then be stored and/or transported to a second location. Moreover, second material can be transported to a final location where it may be used, for example, in an analysis of a material such as a sample or target. Effectively "transporting" and transferring hyperpolarization permits a generic material to be hyperpolarized by individuals that have made an investment in capital equipment, and to then transport that hyperpolarized material to an end user. This creates the significant benefit of the end user not needing to invest in expensive equipment to take advantage of the superior results that may be provided by using hyperpolarized material. Aspects relating to transporting hyperpolarized material are described in detail below.

As further depicted in FIG. 1, an analysis may be performed of a region proximate the target material and/or the target material itself. For example, the analysis may include forming magnetic resonance images of a region of interest, such as of a patient using a commercial MRI scanner (e.g., GE Sigma 1.5 T or 3.0 T scanners) or other scanners such as for research having higher field capabilities (e.g., 7.0 T main field strength) and the like having a main magnet 150 and associated transmit and receive coils/antennas 152 and supporting hardware 154 as known in the art. It will be understood that similar hardware (e.g., imaging coils connected to transmitters and computer controls connected to a scanner, etc.) may be used in accordance with other embodiments of the invention as disclosed herein. By way of further example, the analysis may include analyzing NMR spectra of an in vitro or in vivo sample or target using transmit and/or receive coils as known in the art (not shown). It will be recognized that the depiction of magnet 150 generally refers to a large magnet that applies a steady state magnetic field to a region of interest to be imaged, whether it be for MRI, NMR or other analysis.

When employed for MR imaging applications, hyperpolarized material has a number of advantages over traditional MR contrast agents. Traditional contrast agents contain a paramagnetic compound and operate by influencing the magnetic environment of the surrounding tissue. As many paramagnetic compounds have toxicity concerns there are severe constraints on the use of these for in vivo purposes. Moreover, traditional contrast agents often give rise to "wash out" problems in that their effect cannot be easily controlled. This leads to the production of artifacts in the image.

Because the polarization of a hyperpolarized ("HP") agent is a function of time, its "wash out" effect can be readily accounted for. In addition, the nuclear hyperpolarization of the agent may be destroyed very quickly through application of appropriate electromagnetic pulses, thus eliminating any "wash out" effects. Moreover, the HP agent can be made from nuclei that have very low backgrounds in vivo, giving a very high achievable resolution. Lastly, HP agents may be made from non toxic materials allowing for repeat use without toxicity concerns. Moreover, as described herein, if the hyperpolarized material includes a material that may be metabolized, it is possible to obtain NMR spectra/MR images of such a material as it is metabolized and turned into hyperpolarized metabolites. Traditional contrast agents do not participate in metabolic events. Use of non hyperpolarized materials does not give sufficient signal for the metabolites to be detected by the MRI machine. Thus, use of agents made in accordance with the present invention may directly quantify metabolic activity.

A system 100 for producing a hyperpolarized material is depicted in FIG. 1. System 100 provides a means for providing a first material 112 (which can be any suitable material as described herein provided in any suitable manner, such as a mixture or a component thereof), a means 110 for increasing the nuclear polarization of the first material 112 until the first material becomes hyperpolarized, and means 120 for transferring the hyperpolarization from the first material 112 to second material 122.

Figure 2:
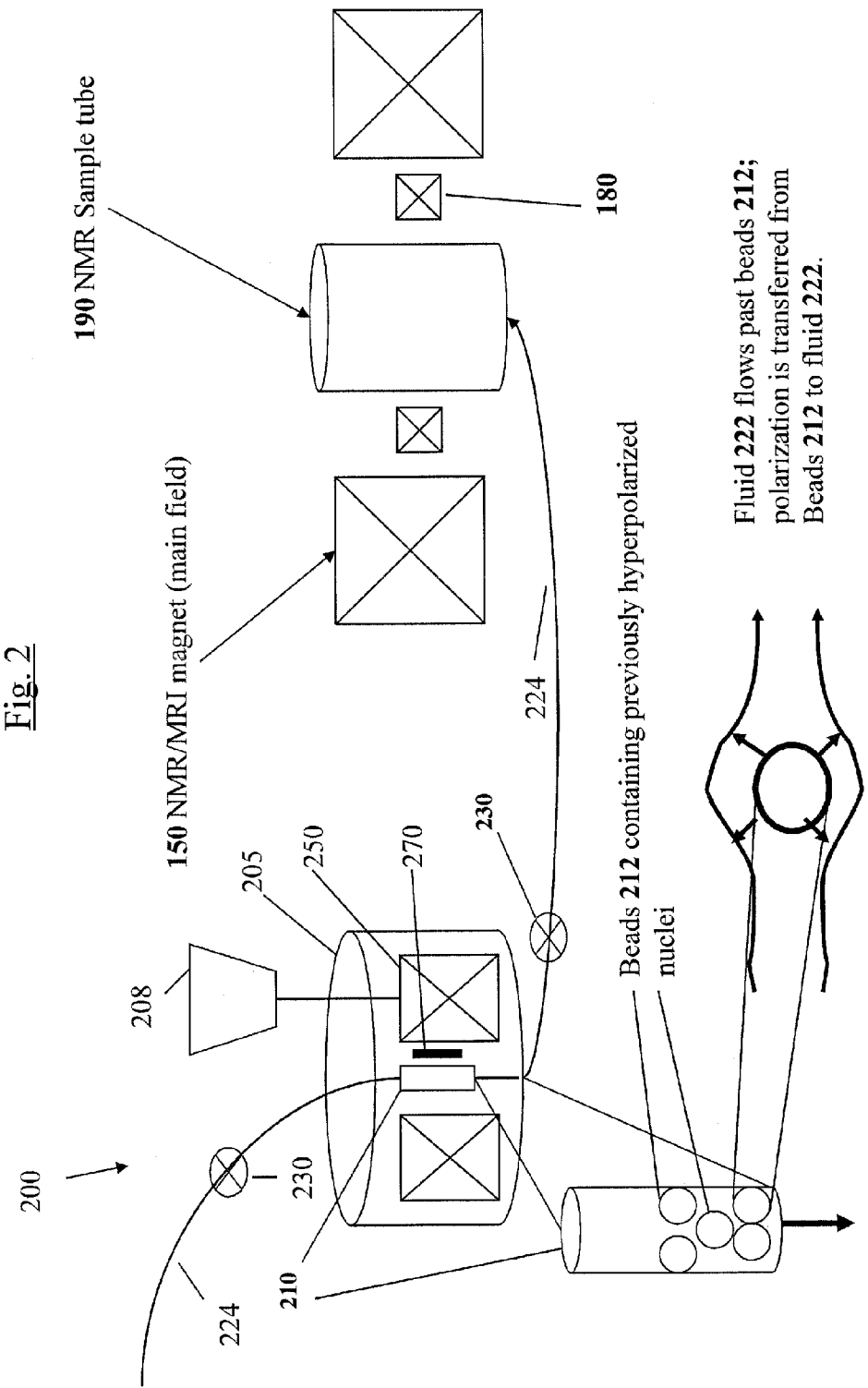
FIG. 2 is a schematic view of a second system made in accordance with the present invention.

For purposes of further illustration and not limitation, as embodied herein and as depicted in FIG. 2, a system 200 is provided for transferring nuclear hyperpolarization via thorough mixing. With reference to FIG. 2, system 200 includes a means for providing a first material 212 such as a container 210 including a plurality of spheres 212 of first material 212, each of which preferably includes hyperpolarized material. It will be recognized that first material 212 may be provided in any suitable high surface area configuration, and that the recitation of a spherical particle bed geometry is merely intended to be exemplary. The first material 212 may be hyperpolarized using any technique embodied herein.

System 200 further includes a container 205 such as a Dewar as known in the art adapted and configured to receive container 210 and having a holding magnet 250 (which may be a permanent magnet, a conventional electromagnet, or a magnet having windings including high temperature or low temperature superconductive materials (HTS/LTS materials) for applying a magnetic holding field, such as a magnetic dipole, about the particle bed 210 to help maintain hyperpolarization of material in the spheres. A source 208 of coolant and electrical power, if required, for the magnet 250 may be provided.

A stream of second material 222 in fluid form is directed over bed 210 by a fluid source 220 in communication with a conduit 224 by operation of valves 230. Second material 222 may be provided as a gas or liquid passing over first material 212, creating physical contact between the two materials, permitting a transfer of hyperpolarization. If desired, RF pulses may be applied to help facilitate the transfer of hyperpolarization as described herein. The hyperpolarized second material 222 may then be further directed through conduit 224 to NMR sample tube 190 or a patient (not shown) and MRI/NMR analyses can be performed as described herein.

A variety of other configurations can be provided for transferring hyperpolarization thorough mixing. For example, the particle bed could include material that can be quickly melted by a heater 270, for example, and dispersed through the second material. The materials may further be caused to mix by causing them to flow over a series of obstructions made preferably, though not exclusively, from reasonably non depolarizing material such as PTFE coated glass.

Figure 3:
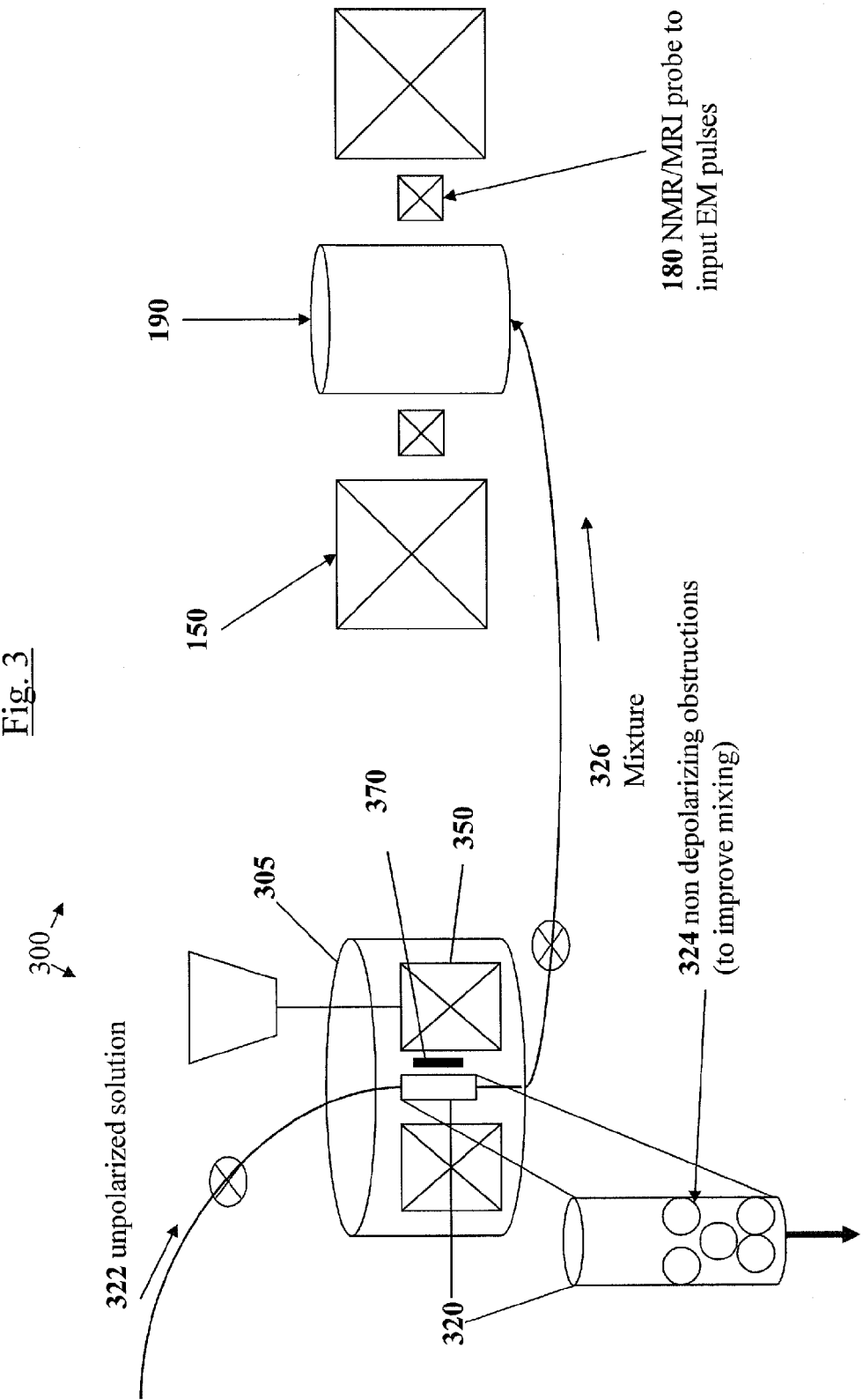
FIG. 3 is a schematic view of a third system made in accordance with the present invention.

By way of further example, FIG. 3 depicts an exemplary system 300 for transferring hyperpolarization using electromagnetic coupling. In this example a frozen hyperpolarized material 312 is melted and dispersed into a previously unpolarized solution 322 in a container 320 inside of a refrigerated container 305 having a holding field provided by a magnet 350 whose solvent is chemically identical to the first material. Non depolarizing flow obstructions 324 may be provided to promote mixing of the polarized and unpolarized material. Optionally, the magnetic field of magnet 350 may be of sufficient homogeneity to provide for good RF pulses of appropriate frequency and magnitude to be applied to the mixture. If desired, a heater 370 may provide heat to promote melting of the frozen material 312. By application of pressure, the mixed solution 326 is caused to flow into the bore of a system having a magnet 150 and a probe 160 (similar in concept to components 152, 154 described above) suitable for application of RF pulses. RF pulses, typically selected to excite the resonance line of the hyperpolarized nuclei, are applied to cause spin flip transitions between the nuclei in the melted solvent and the spins in the analyte. As will be appreciated, system 300 may be suitably adapted for in vivo MRI studies.

In further accordance with the invention, a method and system of producing a hyperpolarized material is provided. The method includes providing a solvent, hyperpolarizing the solvent, and transferring hyperpolarization from the solvent to a target material. The system provides the necessary components to carry out the steps of the method. Accordingly a hyperpolarized solvent is also provided.

In accordance with a further aspect, the solvent and target material may be hyperpolarized after they are mixed. If desired, the solvent and/or target material may each be composed of a plurality of component materials that are mixed together. These component materials may be hyperpolarized prior to mixture, during mixture or after mixture.

For purposes of illustration and not limitation, as embodied herein, the solvent may include a liquid suitable for in vitro NMR analysis. For example, the solvent may include a material selected from the group including water, deuterated water, acetone-$d_6$, ethanol-$d_6$, acetonitrile-$d_3$, formic acid-$d_2$, benzene-$d_6$, methanol-$d_4$, chloroform-$d_1$, nitromethane-$d_3$, deuterium oxide, pyridine-$d_5$, dichloromethane-$d_2$, 1,1,2,2-tetrachloroethane-$d_2$, dimethylformamide-$d_7$, tetrahydrofurane-$d_8$, dimethylsulfoxide-$d_6$, toluene-$d_8$, 1,4-dioxane-$d_8$, trifluoroacetic acid-$d_1$ and combinations thereof. By way of further example, the solvent may include a physiologically tolerable liquid suitable for use in in vivo MRI studies. Physiologically tolerable solvents include water, saline and the like.

The molecules of the solvent itself may be hyperpolarized, for example, by way of a technique selected from the group including (i) dynamic nuclear polarization, (ii) the Nuclear Overhauser effect, (ii) parahydrogen induced polarization, (iii) hyperpolarization using a quantum relaxation switch, (iv) transferring hyperpolarization to molecules of the solvent by exposing them to hyperpolarized nuclei of a previously hyperpolarized gas, and combinations thereof.

In accordance with still a further aspect, the method may further include arranging the solvent into a high surface area configuration prior to being hyperpolarized. This can be particularly advantageous when practicing the QRS method for achieving hyperpolarization.

Figure 4:
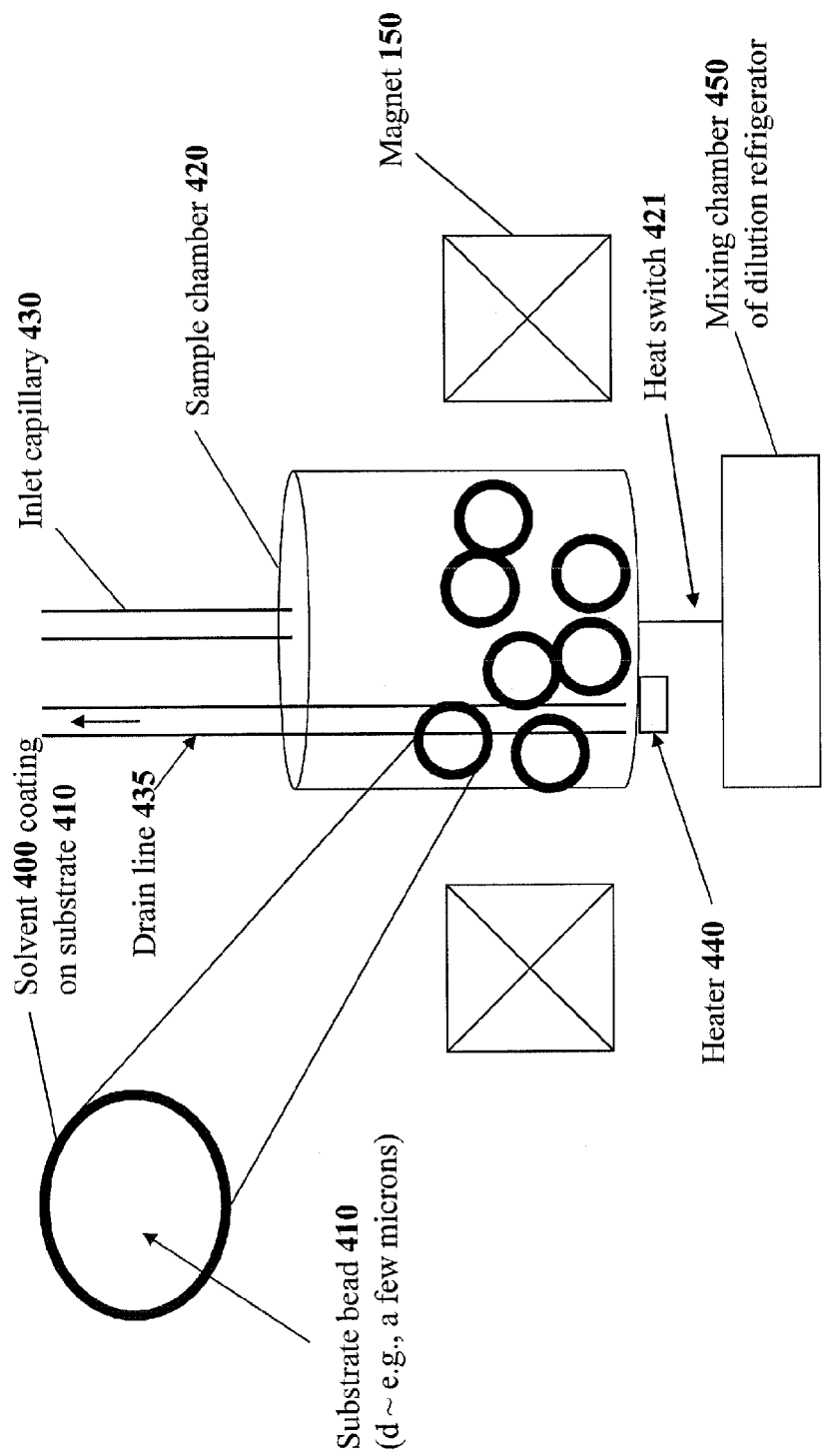
FIG. 4 is a schematic view of a fourth system made in accordance with the present invention.

For example, as depicted in FIG. 4, the solvent 400 may be arranged into a high surface area configuration by distributing the solvent onto a high surface area substrate 410 prior to being hyperpolarized. The high surface area substrate 410 may include, for example, an aerogel material, silicon beads, fumed silica, carbon nanostructures, silicon nanofibers, exfoliated carbon and combinations thereof, among others.

The high surface area substrate 410 is preferably arranged in a sample chamber 420 adapted and configured to contain the material. Any suitable method may be used to hyperpolarize the solvent, such as a brute force method as described herein making use of a quantum relaxation switch employing $^3$He, among other techniques. Accordingly, a magnet 150 may be used to expose the sample to a high magnetic field, and sample chamber 420 may be maintained at extremely low temperatures (such as below 1.0K) to create the brute force environment. Good thermal contact between the sample chamber 420 and the cold section of a refrigeration mechanism, such as the mixing chamber 450 of a dilution refrigerator, is provided by a heat switch 421. $^3$He may be added to the chamber to facilitate hyperpolarization of the sample, and $^4$He may be subsequently added to remove the $^3$He to allow the sample to be warmed without undue loss of polarization. The solvent and/or other fluids may be delivered into chamber by way of inlet capillary 430. Fluids may exit chamber 420 by way of drain line 435. After the solvent is hyperpolarized, a heat switch/heater 440 may be used to melt frozen hyperpolarized solvent 400 from the high surface area substrate 410, and to deliver it to a mixing chamber 450 where the hyperpolarized solvent may be mixed with solvent that has not been hyperpolarized for delivery.

Preferably, the method and system also provides for cleaning the surface of the high surface area substrate 410 of magnetic impurities, such as but not limited to oxygen groups, iron oxides, unpaired electron groups, and the like. In accordance with another aspect, the high surface area substrate is also preferably magnetically inert.

Figure 5:
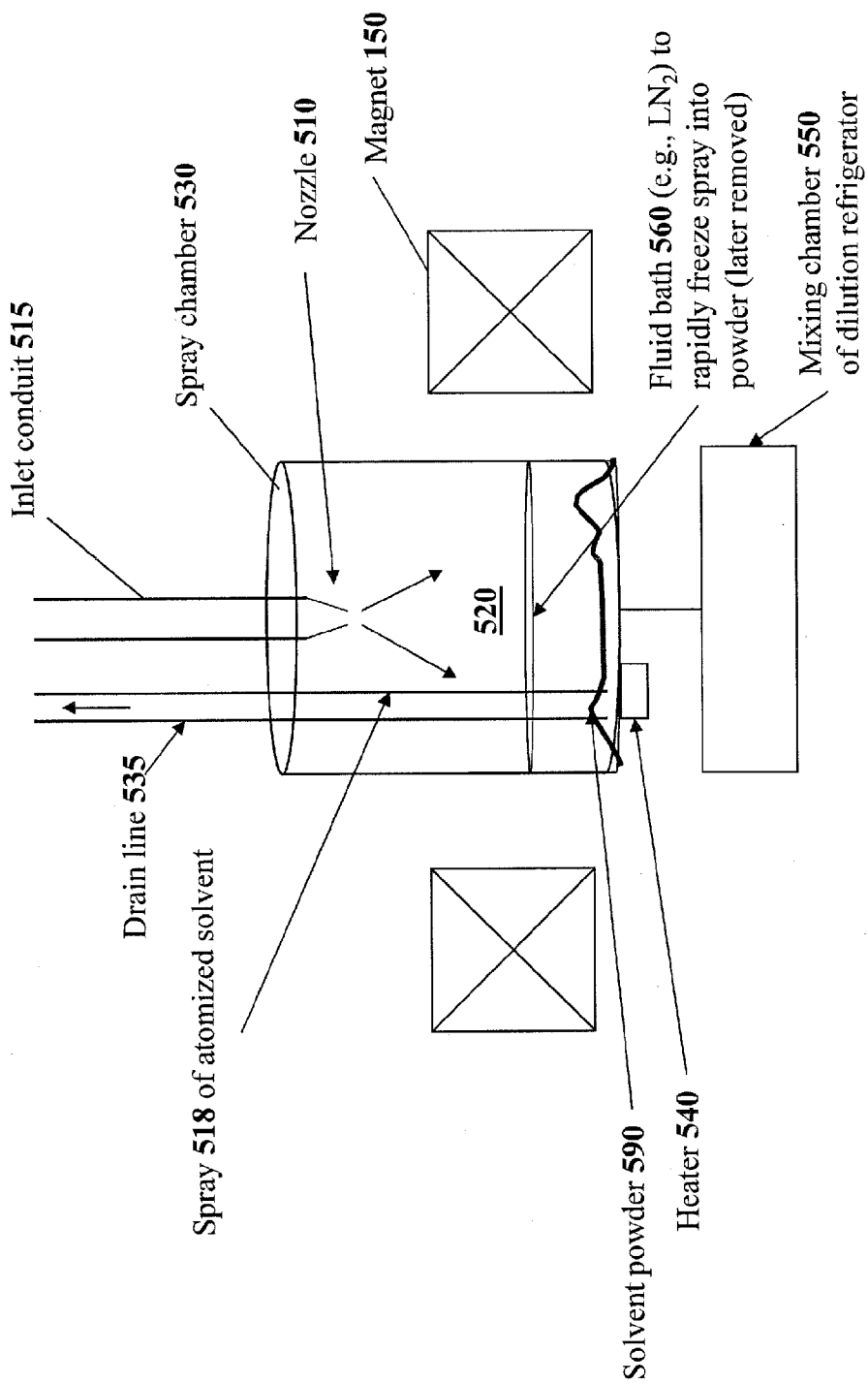
FIG. 5 is a schematic view of a fifth system made in accordance with the present invention.

In accordance with still a further aspect the method may include arranging the solvent into a high surface area configuration by converting the solvent into a finely divided form. For example as depicted in FIG. 5, the solvent 500 may be converted into a powder 590. The spraying operation may be performed, for example, inside of a spray chamber 530, and subsequently freezing the solvent 500 into solvent powder 590. The solvent 500 may be converted into a powder 590, for example, by introducing the solvent through an inlet conduit 515 and atomizing the solvent 500 into a spray 518 from a nozzle 510 in the presence of a cooled atmosphere 520 (provided, for example, by a bath 560 of a cryogenic fluid, such as liquid nitrogen). The cooled atmosphere may later be removed, for example, by simply heating the sample volume for a brief period, leaving the micronized powder 590 ready for hyperpolarization. Accordingly, the solvent may be powderized using methods such as spray freezing into liquid (SFL) or spray condensation (SC) techniques, among others. After the solvent 500 is frozen into a powder 590 form, it may be stored in a frozen state before being hyperpolarized.

If desired, a powder 590 may also be provided formed from a material that is solid at standard conditions. This solid material may be converted into powdered form using any known technique (e.g., grinding, attrition mills, plasma sputtering techniques and the like). The solid material may include any material that can be hyperpolarized, and preferably includes material selected from the group including $^{13}C$, $^{15}N$, $^{1}H$, $^{31}P$, $^{19}F$, $^{29}Si$ and combinations thereof. A solid powdered material 590 may then be hyperpolarized as disclosed herein.

If desired, powder 590 may be hyperpolarized using any methods described herein. Preferably, solvent powder 590 is hyperpolarized using a quantum relaxation switch. If a QRS technique is used, for example, the chamber may be cooled by using a heat switch to facilitate good thermal contact to the cold portion of a low temperature refrigerator such as the mixing chamber of a dilution refrigerator 550. The $^{3}He$ and $^{4}He$ may be introduced into chamber 530, and magnet 150 may be used to facilitate hyperpolarization of the powder 590. By way of further example, the powder may be hyperpolarized using QRS or other technique as described herein in a different apparatus. After the solvent 500 is hyperpolarized, as with the embodiment of FIG. 4, a heater 540 may be used to melt frozen hyperpolarized powder 590, and to deliver it via a drain line 535 to a mixing platform (not shown in FIG. 5) where the hyperpolarized solvent 500 may be mixed with solvent that has not been hyperpolarized for delivery.

Whether the solvent is sprayed and frozen or not, particularly when the QRS method is practiced, the solvent is preferably cooled prior to hyperpolarizing the solvent. In accordance with one embodiment, the solvent is cooled to a temperature below about 100K prior to hyperpolarizing the solvent. More preferably, the method includes cooling the solvent to a temperature below about 80K, 60K, 40K, 20K, 10K, 5K, or even 1K prior to hyperpolarizing the solvent. As a general matter, when materials are cooled, it becomes easier to hyperpolarize them. Specifically, nuclear polarization in a given field is a hyperbolic tangent function $P=\tan h(uB/k_BT)$ Where u=gyromagnetic ratio of nuclei
B=applied magnetic field
$K_B$=Boltzmann's constant
T=temperature From this it can be seen that in general the lower the temperature the higher the degree of polarization that can be achieved in a given magnetic field.

The method may include exposing the solvent to a magnetic field. This can be used to facilitate hyperpolarization of the solvent, particularly when employing the QRS method Moreover, application of a field is necessary for DNP, in order to polarize the electron spins before transfer of polarization to nearby nuclear spins. Typical field strengths in the context of DNP here are from about 1 T to about 3 T. Larger fields are generally not needed as the polarization of the electron spins saturates at these values (at temps ~1.6 K). As will be further appreciated by those of skill in the art, even a small magnetic field (e.g., several hundred Gauss) is used in production of hyperpolarized gases.

As indicated above, hyperpolarization in the brute force/QRS environment increases with increasing magnetic field. At sufficiently high B/T values the relationship becomes linear so that the hyperpolarization ~B/T. In accordance with one embodiment, the strength of the magnetic field is greater than about 10 mT. More preferably, the magnetic field has a strength greater than about 0.5 T, 1.0 T, 1.5 T, 2.0 T, 3.0 T, 5.0 T, 7.0 T, 10.0 T, 15.0 T, 20.0 T or even 25.0 T.

In practicing the QRS method, the solvent is next exposed to $^{3}He$ to facilitate hyperpolarization of the solvent. The solvent is preferably exposed to a sufficient quantity of $^{3}He$ to cause at least a monolayer of $^{3}He$ to form on the solvent. This can be carried out, for example, in accordance with the teachings in U.S. Pat. No. 6,651,459. While that reference discloses hyperpolarizing a frozen gas, the inventors of this patent application have recognized herein that this technique is applicable to frozen liquids as well as other solid materials. Importantly, it is highly desirable for the material to be polarized to be configured to have a high surface area. While this is straightforward when the material is a gas, when the material is a liquid or a solid this is more difficult. In the case of a liquid, a preferred embodiment is that the liquid may be polarized by first atomizing it into submicron sized droplets, for example, as described above. The droplets may be quickly solidified to form a powder. As a second embodiment, the liquid can be caused to adhere to the surface of a substrate such as silica aerogel using surface tension. Excess liquid in the pores of the substrate may be dried so that the pores are largely empty and the liquid forms a layer in the strands less than 5 microns thick. Layers thicker than this can be expected to not polarize quickly during the QRS process.

In the case of a solid, the solid is preferably powderized until the typical diameter of a particle in the powder is less than about 5 microns. Particles substantially larger than this can be expected to not polarize quickly during the QRS process.

The QRS process requires operation in a regime of low temperature and preferably, high magnetic field. Moreover, structural elements such as capillary lines may be provided that are capable of allowing introduction of $^{3}He$ and $^{4}He$ to the material(s) to be hyperpolarized in appropriate amounts and at appropriate steps in the process. It will be appreciated that the capillary lines must be carefully constructed to minimize heat loading into the sample region.

In the case of QRS, the solvent is then maintained at a cooled temperature in a magnetic field for a time sufficient to permit relaxation of a substantial portion of the solvent into a state of hyperpolarization. Similarly, in a DNP process, the amount of hyperpolarization improves with increasing time, but while applying microwaves to the material to be polarized. In the case of employing QRS, for example, the time sufficient to permit relaxation may vary between several hours or even several days, as appropriate, in any time increment. Furthermore, when employing the QRS method, the frozen hyperpolarized solvent is further exposed to $^4$He to displace the $^3$He from the solvent.

As will be further appreciated by those of skill in the art, in addition to processing a solvent, it is also possible to dissolve an analyte in a solvent to make a solution and powderize it as described herein. This powder can also become hyperpolarized in accordance with the invention. As such, in accordance with the invention, it is possible to powderize any liquid and/or solution for the purposes of making a hyperpolarized solution as well as a hyperpolarized suspension, emulsion, colloid, and composite material or component thereof, as described herein.

Regardless of how it has been hyperpolarized, once hyperpolarized, the solvent is in a condition where it may be stored for extended periods of time. Maintenance of the hyperpolarization is facilitated by storing the hyperpolarized solution in a magnetic field and/or at low temperatures, for example, in a Dewar container (e.g., 305) as described herein that is able to maintain a magnetic holding field. Generally, for purposes of storage and/or transport of hyperpolarized material, application of a magnetic field at least in excess of 1G and maintenance of a low temperature environment are preferred.

Moreover, once frozen and in a substantially stable state of hyperpolarization, the solvent may be transported in a container (e.g., 305, 605 as described herein) from a first location to a second location. The hyperpolarized solvent may be used at the second location, or may be stored at the second location. For example, the frozen hyperpolarized solvent may be maintained in an inventory until it is ordered for purchase by an end user and then delivered to the end user at a third location. It will be recognized that these teachings of storing and transporting hyperpolarized material to storage and/or an end user applies to all hyperpolarized materials described herein, regardless as to how the material is put into a state of hyperpolarization.

Any of a variety of containers may be used for storing and/or transporting hyperpolarized material. As will be appreciated, FIG. 6 shows how such an exemplary container 605 can be configured for storing/transporting hyperpolarized materials to a customer site and how the hyperpolarized material may be accessed to facilitate an NMR or MRI study. As depicted in FIG. 6, a storage vessel 605 comprising, for example, a vacuum insulated Dewar may be provided for storing and transporting a stabilized hyperpolarized material 600. It will be understood from the figure that the design of the Dewar is to allow a hyperpolarized material to be maintained at a low temperature while in an adequate magnetic field, the purpose of which is to allow the hyperpolarization of the material to be retained during transport/storage for as long a time as possible.

Preferably, vessel 605 includes a sealed chamber 620 for isolating the material 600 from the environment, a first means for maintaining a depressed temperature 630, such as a portable cryocooler and/or a bath of liquid cryogenic fluid (e.g., $LN_2$ and the like), and a means (e.g., a magnet) 640 for maintaining a magnetic field about the material 600.

Various cryogenic fluids may be used to maintain a depressed temperature, such as liquid helium, liquid hydrogen, liquid neon, liquid nitrogen, liquid argon, liquid oxygen, liquid carbon dioxide, and the like. Additionally or alternatively, a transportable cryocooler can be used to maintain temperatures as low as 4 K in the sample region. The design and construction of such lightweight cryocoolers are well understood in the art and commercially available. Moreover, materials with very high specific heats at low temperatures may be loaded inside the cryostat to keep the hyperpolarized material cooled during storage/transport.

Besides application of low temperatures and magnetic fields, various techniques for extending the lifetime of nuclear polarization have been described in the literature. For example, it is known that singlet states often have longer lifetimes—sometimes as much as 10 times longer—than the standard $T_1$ of the spin ensemble. As described in Caravetta and Levitt, Journal of Chemical Physics 122, 2145059 (2005), pulse sequences can be formulated to load the nuclear polarization of a dipolar coupled system of ½ spins into its singlet state. The singlet state itself is undetectable using NMR but the resultant spin order can be recaptured after a time by application of further RF pulses. As such, these and other techniques known in the art for extending the lifetime of nuclear polarization may be employed with any of the methods and systems of the invention described herein.

Magnet 640 may be a permanent magnet, or a solenoidal configuration made either from superconducting and/or "normal" non superconducting wire. If desired, magnet 640 can be configured to have a higher than standard homogeneity to permit efficient application of RF pulses to materials contained in its interior. It will be appreciated that many superconducting materials used as windings are integrated with conventional conducting material to permit transition to the superconducting state, whereby electrons will begin flowing through the superconducting material at a point where the superconducting material can carry the given current density provided that the particular temperature and background magnetic field are both low enough to permit a superconducting state. For ease of use, a solenoidal or permanent magnet configuration could also be made so as to minimize the creation of stray field outside the sample region.

The magnetic field in the sample region should be sufficient to freeze out as much as possible events that cause transitions between the nuclei from up to down states or vice versa, particularly to minimize Zeeman transitions. In addition, optionally, one may use magnetic screening to minimize access of depolarizing radiation to the hyperpolarized material or materials. For example, it is within the scope of the invention to employ a material, such as Mu-Metal as a shield to prevent events that cause nuclei to lose their polarization. Mu-metal is a nickel-iron alloy (75% nickel, 15% iron, plus copper and molybdenum) that has a very high magnetic permeability. The high permeability makes Mu-metal very effective at screening static or low-frequency magnetic fields, which cannot be attenuated by other methods.

Moreover, where a hyperpolarized material is provided that may be later liquefied for use, the material 600 may be disposed in the pathway of a conduit 650. Conduit includes an input end 652 and input valve 656 for receiving a flow of material, and a discharge end 654 with a discharge valve 658 for directing a mixture of the material and the hyperpolarized material 600 to an end location for use. Stated another way, conduit 650 may be used to "flush" the hyperpolarized material through vessel 610 in order to use it. The conduit 650 should be made from material that is as non depolarizing as possible such as Teflon or polyethylene. Valves 656, 658 are preferably also made from non depolarizing material.

When a user, such as a customer wishes to perform an NMR study, the user first preferably makes a solution from a solvent identical to the one in the sample region and the analyte of interest. The user would use less solvent than normal as the rest will be made up from the frozen hyperpolarized solvent contained in the sample region. Next, the user attaches the end of his sample outlet line to the open end of valve 656 that seals input end 652. The user attaches the inlet line to his or her NMR sample tube (e.g., 190 described herein) to the open end of valve 658 that seals output end 654.

By exerting slight pressure on their sample, for example via use of a syringe or other pressure source (e.g., compressed gas and the like) or even the pressure from heating the sample in the container 605, by opening valve 656, the user's sample flows through the sample region. Heater 670 is used to melt the polarized solvent in the sample region. The two solvents are mixed together by using slight pressure to drive them through a mixing region, such as a small volume having a narrowed diameter that causes the unpolarized solvent and polarized solvent to thoroughly mix. This increases the overall hyperpolarization of the mixture that is then driven into the NMR region by continued application of pressure from the syringe.

U.S. Pat. No. 5,642,625 describes the use of low temperatures to extend the lifetime of hyperpolarized xenon at cryogenic temperatures. U.S. Pat. No. 7,066,319 describes a transport Dewar to facilitate transport of hyperpolarized gas by application of a magnetic field. U.S. Pat. No. 6,807,810 describes a method of minimizing polarization loss in transported hyperpolarized gases by exclusion of stray RF fields. U.S. Pat. No. 5,612,103 describes the use of specialized coatings to minimize polarization loss during transportation or storage of a hyperpolarized gas. Each of these patents is incorporated by reference herein in its entirety.

In U.S. Pat. No. 6,466,814 ("the '814 patent"), a method of producing a hyperpolarized solution is described wherein a high T1 agent is first polarized and then dissolved in a solvent. This patent is also incorporated by reference herein in its entirety. This method has a number of drawbacks.

As a first example, the hyperpolarization is limited by the T1 of the agent in the '814 patent. By hyperpolarizing a solvent first as with certain embodiments disclosed herein, the longer T1s available in certain solvents can be used to enhance the overall hyperpolarization of a product that may be manufactured.

As a second example, the method in the '814 patent describes a method that requires exposing a material to be hyperpolarized to low temperatures. In various aspects of the invention disclosed herein, it is possible to hyperpolarize a medium, warm the medium to room temperature, mix the analyte in the medium at room temperature and send the mixture for NMR analysis, MR imaging and/or to transfer hyperpolarization from the medium to the analyte. By freezing the medium instead of the analyte, it is possible to analyze materials that would be damaged or destroyed by freezing, such as cells or other biological organisms that could rupture, among other things. Moreover, while the '814 patent teaches hyperpolarization of the analyte by DNP and the brute force technique (low temperature, high field, extended time periods), it fails to teach use of a quantum relaxation switch in combination with the brute force environment.

In addition, the method described in '814 polarizes the analyte or target material, whereas the method disclosed herein polarizes the solvent and then transfers polarization to the analyte. This approach has significant advantages for transportation of hyperpolarized materials in that it allows for the selection of a solvent that has a very long $T_1$ both in solidified and liquid form.

In addition, the solvent in a typical NMR/MRI study typically has far more spins than the analyte of interest. By polarizing the solvent a large ensemble of polarized spins is made available for transfer to the analyte. This transfer can be used to extend the time over which the NMR/MRI operation may be performed. Under appropriate conditions, this technique can also be used to allow site selective transfer of polarization to analyte nuclei of interest.

Moreover, as described herein, the QRS method does not require use of a trityl radical, and it is also scalable. Also, by hyperpolarizing a solvent first as discussed herein, and then transferring hyperpolarization to the analyte, an added benefit is provided in that it is possible to transfer the hyperpolarized solution to an end location such as an NMR magnet or into a region of interest such as a patient with a minimum of polarization loss.

By way of further example, by providing ready access to many hyperpolarized solvents, it is possible to avoid the necessity of using RF pulses to transfer polarization from one material to the other. For example, employing RF pulses to transfer polarization using a material disposed in hyperpolarized liquid Xenon, while possible, is not easily accomplished, and may result in artifacts in NMR data that need to be accounted for. In contrast, in accordance with some of the embodiments disclosed herein, by providing a hyperpolarized solvent having nuclei identical to those in the solute, hyperpolarization transfer may be accomplished from solvent to solute by spin diffusion which requires no RF pulses or does not produce unwanted artifacts in the end data. As such, the present invention also provides hyperpolarized solvents in addition to Xenon that may be used to transfer hyperpolarization to an unpolarized material that contains nuclei that are preferably the same or substantially the same material as the solvent so as to facilitate transfer of polarization via spin diffusion.

However, it will be appreciated that Xenon may be used in accordance with the invention as a first material that may be hyperpolarized and used to hyperpolarize a second material in a variety of contexts, as discussed herein. For example, Xenon may be used as a hyperpolarization carrier to help hyperpolarize a core portion of an encapsulated agent having a porous encapsulating layer as described elsewhere herein. More generally, Xenon may be used as a first hyperpolarized material that can be used to hyperpolarize a second material that, in turn, is transported to another location to be used in studies or for other reasons.

For all of the methods described in the above patents, delivery of the hyperpolarized material can be accomplished, for example, only by warming up the hyperpolarized material and then flushing it from the transport container. By contrast, the utilization of a hyperpolarized solvent requires not only that the hyperpolarization of the solvent survive the trip to the customer's site but that melting of the HP solvent be correlated with the input of unpolarized solvent to the sample region as well as to the customer's NMR magnet. In addition, to ensure efficient transfer of hyperpolarization to the customer's analyte requires that the customer's original solution and the melted polarized solvent be mixed as quickly and as thoroughly as possible. Without this, the hyperpolarization may become greatly diminished. As such, there is a significant need for a container that can transport hyperpolarized solvents and accomplish thorough mixing of the unpolarized solution and the melted polarized solvent when an NMR/MRI study is ready to be performed.

It will be understood that, if desired, the transport container could be used to transport previously mixed solutions manufactured in a manner distinct from that described in U.S. Pat. No. 6,466,814. In this case, the entire solution is transported to the site of interest. When it is desired to perform an NMR/MRI study, the solution may be warmed and introduced either into the sample region of the NMR magnet (for in vitro NMR purposes) or in vivo, e.g., to a patient (for in vivo MRI purposes).

Once the hyperpolarized solvent has been transported to a location where it will be used, the hyperpolarized solvent may be mixed with a material, such as a sample to be analyzed. Any of a variety of end users are possible, including research institutions, hospitals, universities, imaging clinics, drug development laboratories, contract NMR research facilities and the like. This can be carried out in a variety of ways. For example, if a frozen liquid, the hyperpolarized solvent may be mixed with additional unpolarized solvent in liquid form to form a solvent mixture as described in detail above. The unpolarized solvent may contain the analyte of interest already dissolved in it. Alternatively, the mixture of unpolarized and polarized solvent may be directed to a container with the analyte, so that the analyte dissolves into the mixture of polarized and unpolarized solvent; the resulting solution and/or suspension, colloid, emulsion etc may then be directed to the NMR magnet for analysis. Alternatively, no unpolarized solution may be added to the polarized solvent, the polarized solvent is warmed and directed to a container with the analyte of interest, the resulting solution and/or suspension, colloid, emulsion etc may then be directed to the NMR magnet for analysis. As such, conduit 650 of vessel 605 described above can be used to deliver a stream of unpolarized material over frozen hyperpolarized material 600, thereby creating a mixture containing hyperpolarized material, which can then be used for in vivo MRI or in vitro NMR analysis.

In using the hyperpolarized solvent for analysis, it is generally desirable to increase the temperature of the material so that it may be used. Preferably, the temperature of the hyperpolarized solvent is increased in the presence of a magnetic field having a strength greater than about 1.0 Gauss. A good example of an embodiment of this aspect of the method can be demonstrate by use of vessel 605, which preferably includes a means 640 for providing a magnetic field. By way of further example, any vessel used to transport the hyperpolarized solvent may be disposed in a magnetic field to facilitate this embodiment of the invention.

Even more preferably, the temperature of the hyperpolarized solvent is increased in the presence of a magnetic field having a strength greater than about 1.0, 1.5, 3.0, 7.0 Tesla or even 10.0 Tesla. The solvent is preferably increased in temperature within a time sufficient to avoid substantial loss of hyperpolarization. If desired, the temperature of the solvent may be increased to room temperature. If desired, the hyperpolarized solvent may be eluted from the high surface area substrate, in the event the solution was initially frozen and hyperpolarized over a high temperature substrate. By way of further example, if the solution is frozen by spray freezing as described herein, the frozen particulate may just be melted. As a general matter, raising the temperature of the hyperpolarized solvent in the presence of a higher field will generally preserve hyperpolarization better than a weaker field will, with all other variables remaining constant.

By way of further example, once the hyperpolarized solvent has been provided, it may be mixed with a target material to create a mixture, such as (i) a solution, (ii) a suspension, (iii) an emulsion, (iv) a colloid and (v) a composite material, among others. These could be solutions made from pyruvate in water or saline, suspensions made from composite materials as described herein, hyperpolarized hexafluorobenzene or other halogens suspended directly in water/saline or another physiologically tolerable fluid, suspensions of solid particles in air or another gas for inhalation therapy purpose, among others. Emulsions may be made from Propofol or Diprivan or other emulsions typically suitable for use in vivo. Colloids may be colloidal silver or keratinous protein, or Tc-99m sulfur, and the like. Composite materials may be two phase encapsulated agents such as encapsulated decafluorobutane gas, and the like.

Upon mixing the target material with the hyperpolarized solution, if desired, it is possible to transfer hyperpolarization to the target material. As a first example, the target material may be hyperpolarized by way of thorough mixing as described above. Moreover, the target material may be hyperpolarized by way of electromagnetic coupling as described above.

Hyperpolarized solvents may accordingly be used to hyperpolarize a target material to facilitate analysis thereof. Thus, in contrast to prior art techniques, such as those described in U.S. Pat. No. 6,466,814, which is incorporated herein by reference in its entirety, the solvent in the present invention is polarized and then used to hyperpolarize a material to be analyzed, as opposed to introducing hyperpolarized particulate into a non-hyperpolarized solvent to provide a hyperpolarized solution. As such, using the hyperpolarized solvent of the invention, it is possible to facilitate analysis of a material to be analyzed using NMR spectroscopy, or by way of MR imaging. A hyperpolarized solvent can be used to greatly speed analysis of a material to be analyzed, or to facilitate performing an study on a sample that was previously of too low a concentration to be detectable in an NMR protocol. In addition, by storing hyperpolarization in the solvent (which can be selected to have a relatively long T1 relaxation time), it is possible to use the benefits of hyperpolarization on a wide variety of materials.

In still further accordance with the invention, a system and method for making a hyperpolarized suspension are provided as well as the hyperpolarized suspension itself.

In still further accordance with the invention, a method of making a hyperpolarized suspension is provided as well as the hyperpolarized suspension itself. The method includes providing a hyperpolarized material and dispersing the hyperpolarized material in a medium to create a hyperpolarized suspension. By way of further example, a hyperpolarized suspension may be provided by hyperpolarizing a medium and dispersing a material in the medium to create a hyperpolarized suspension. Moreover, a hyperpolarized suspension may be made by making a suspension from non-hyperpolarized components, and hyperpolarizing the suspension after it is made. Also, a suspension may be provided that is composed of more than two components, wherein one or more of the components of the suspension are hyperpolarized prior to mixing them.

The hyperpolarized material used to make the suspension may be hyperpolarized using any technique disclosed herein, such as (i) dynamic nuclear polarization, (ii) the Nuclear Overhauser effect, (ii) parahydrogen induced polarization, (iii) hyperpolarization using a quantum relaxation switch, and (iv) transferring hyperpolarization to molecules of the material by exposing them to hyperpolarized nuclei of a previously hyperpolarized gas and combinations thereof.

The hyperpolarized material used to make the suspension is preferably provided in a particulate form, having an average diameter of less than about one thousand microns. More preferably, the hyperpolarized material has a diameter of less than about one hundred microns. Even more preferably, the hyperpolarized material has a diameter of less than about ten microns, five microns or one micron. Preferably, the medium is a physiologically tolerable medium, as illustrated above herein.

Preferably, the hyperpolarized material is dispersed in the medium to create the suspension in the presence of a magnetic field. The magnetic field may have a field strength in excess of 1.0 Gauss. In accordance with still a further aspect, the medium may be selected from the group including (i) a solid, (ii) a liquid and (iii) a gas. For example, the medium may be air. Accordingly, if desired, the method may further include introducing the hyperpolarized suspension into a region of interest such as the respiratory tract of the patient. Materials that may be suspended include, for example, powdered danizol, powdered insulin, and other powdered APIs and/or excipients, among others.

Preferably, the system further includes means for transporting the hyperpolarized suspension from a first location to a second location, similar to the hyperpolarized solvent above, such as a container similar to container 605. As such, it will be appreciated that the hyperpolarized suspension may be made at the same location as the location where the hyperpolarized material is initially hyperpolarized, or a different location, such as at a production facility, or at the location of an end user, such as a hospital or clinic.

In further accordance with the invention, a method of making a hyperpolarized emulsion is provided, as well as the hyperpolarized emulsion itself. The method includes providing a hyperpolarized material, and mixing the hyperpolarized material with a medium to create a hyperpolarized emulsion. The method may alternatively include hyperpolarizing a medium and mixing a material into the medium to create a hyperpolarized emulsion. Moreover, a hyperpolarized emulsion may be made by making an emulsion from non-hyperpolarized components, and hyperpolarizing the emulsion after it is made. Also, an emulsion may be provided that is composed of more than two components, wherein one or more of the components of the emulsion are hyperpolarized prior to mixing them.

For purposes of illustration and not limitation, as embodied herein, a hyperpolarized material is provided, which is then mixed with a medium to create a hyperpolarized emulsion. The hyperpolarized material may be hyperpolarized using a technique selected from the group including (i) dynamic nuclear polarization, (ii) the Nuclear Overhauser effect, (ii) parahydrogen induced polarization, (iii) hyperpolarization using a quantum relaxation switch, and (iv) transferring hyperpolarization to molecules of the material by exposing them to hyperpolarized nuclei of a previously hyperpolarized gas and combinations thereof. Preferably, the medium is a physiologically tolerable medium.

The mixing of the hyperpolarized material and medium preferably takes place in the presence of a magnetic field having a strength of at least about 1.0 Gauss. Moreover, the mixing step preferably takes place at a temperature at which the hyperpolarized material and medium are both in a liquid form. However, if desired, the either hyperpolarized material and medium may be in a solid, liquid or gaseous form when they are mixed. Emulsions might be made, for example, from Propofol or Diprivan or other emulsions typically suitable for use in vivo. Various hardware used to create mixtures using solutions described above and transporting hyperpolarized materials may also be employed in practicing this aspect of the invention.

In further accordance with the invention, a method of making a hyperpolarized colloid is provided as well as the hyperpolarized colloid itself. The method includes providing a hyperpolarized material, and mixing the hyperpolarized material with a medium to create a hyperpolarized colloid. The method may alternatively include hyperpolarizing a medium and mixing a material into the medium to create a hyperpolarized colloid. Moreover, a hyperpolarized colloid may be made by making a colloid from non-hyperpolarized components, and hyperpolarizing the colloid after it is made. Also, a colloid may be provided that is composed of more than two components, wherein one or more of the components of the colloid are hyperpolarized prior to mixing them.

For purposes of illustration and not limitation, as embodied herein, a hyperpolarized material is first provided that is mixed with a medium to create a hyperpolarized colloid. As will be appreciated, a colloid generally includes a system of particles with linear dimensions in the range of about $1 \times 10^{-7}$ to $5 \times 10^{-5}$ cm dispersed in a continuous gaseous, liquid, or solid medium whose properties depend on the large specific surface area. The particles can be large molecules like proteins, or solid, liquid, or gaseous aggregates. The particles generally remain dispersed indefinitely. Examples include colloidal silver or keratinous protein, or Tc-99m sulfur, among others.

The hyperpolarized material may be hyperpolarized using any of the techniques described herein. Moreover, the medium is preferably a physiologically tolerable medium.

In accordance with a further aspect, the mixing step may take place in the presence of a magnetic field, such as one having a strength of at least about 1.0 Gauss. In accordance with yet a further aspect, a system for making a hyperpolarized colloid is provided. The system includes means for providing a hyperpolarized material, and means for mixing the hyperpolarized material with a medium to create a hyperpolarized colloid. If desired, the system may further include means for transporting the hyperpolarized colloid from a first location to a second location, as described herein. Various hardware used to create mixtures using solutions described above and transporting hyperpolarized materials may also be employed in practicing this aspect of the invention.

In further accordance with the invention, a method and system of making a hyperpolarized composite material is provided, as well as the hyperpolarized composite material made in accordance with the method. The method includes providing a hyperpolarized material, and mixing the hyperpolarized material with a medium to create a hyperpolarized composite material. The method may alternatively include hyperpolarizing a medium and mixing a material into the medium to create a hyperpolarized composite material. Moreover, a hyperpolarized composite material may be made by making a composite material from non-hyperpolarized components, and hyperpolarizing the composite material after it is made. Also, a composite material may be provided that is composed of more than two components, wherein one or more of the components of the composite material are hyperpolarized prior to mixing them. The system includes means for carrying out each aspect of the method. Various hardware used to create mixtures using solutions described above and transporting hyperpolarized materials may also be employed in practicing this aspect of the invention as well.

The hyperpolarized composite material may be produced, for example, by providing a hyperpolarized material, and mixing the hyperpolarized material with a medium to create a hyperpolarized composite material. The hyperpolarized material may be produced using any of the techniques described herein. Preferably, the medium is a physiologically tolerable medium.

In accordance with still a further aspect, the mixing step may take place in the presence of a magnetic field. Preferably, the magnetic field has a strength of at least about 1.0 Gauss. The hyperpolarized material may be selected from the group including (i) a solid material, (ii) a liquid material, (iii) a gaseous material and combinations thereof. The medium may be any suitable medium for forming a hyperpolarized composite material, such as water and saline, among others.

In further accordance with the invention, a beneficial agent is provided. The beneficial agent includes a hyperpolarized core material surrounded by a porous encapsulating medium.

For purposes of illustration and not limitation, as embodied herein and as depicted in FIGS. 7(A)-7(F), a method and system are provided for preparing a beneficial agent 700 having an encapsulating layer or medium, 710 and a core portion 720.

The porosity of the encapsulating medium 710 may substantially permit passage of gas through the encapsulating medium to the core material 720. For example, the porosity of the encapsulating medium 710 may substantially permit passage of helium through the encapsulating medium, but may also substantially prohibit passage of gas molecules through the encapsulating medium larger than helium. This can be particularly useful when a technique such as QRS is used to hyperpolarize the core material, as the $^3$He and $^4$He may pass into the core 720 to help hyperpolarize it. The $^3$He may be allowed to pass through the encapsulating material either before or after cooling and in either gas or liquid form. The superfluid $^4$He is most advantageously applied after the material is cooled and hyperpolarized and is therefore in liquid form only.

In accordance with still a further aspect, the hyperpolarized core material may have a relatively long spin-lattice relaxation time. For example, the hyperpolarized core material may include material containing nuclei selected from the group including $^{13}$C, $^{15}$N, $^1$H, 2H, $^{31}$P, $^{19}$F, $^{29}$Si and combinations thereof, among others.

In accordance with still another aspect, the encapsulating medium may include polymeric material. The polymeric material may include a material selected from the group including polytetrafluoroethylene, poly(lactic-co-glycolic acid), polyanhydrides, polyorthoesters, polyvinylalchols, and combinations thereof. Preferably, the encapsulating medium is adapted and configured to substantially maintain its structural integrity at temperatures below 100K, 10K and 1K, if desired. By way of further example, the encapsulating material may also include hyperpolarized material.

In accordance with a further aspect, the hyperpolarized core material may include material that is solid at standard conditions. The term "standard conditions" as used herein is intended to convey conditions of room temperature (about 60 to about 80 degrees Fahrenheit) and atmospheric pressure (about one atmosphere).

The hyperpolarized core material may include material that is liquid, gaseous or solid at standard conditions. If desired, the beneficial agent may be provided in the form of a capsule having an average diameter between about 0.001 microns and about 100 microns. Preferably, the beneficial agent is provided in the form of a capsule having an average diameter between about 0.001 microns and about 10 microns. Particularly advantageous size ranges are those that allow for the capsules to pass through small in vivo capillaries (several microns or less) that speed penetration across the blood brain barrier or into any other tissue type.

As a non exclusive example, decafluorobutane gas encapsulated in porous microparticles are currently in advanced FDA trials for use as in ultrasound imaging protocols. In accordance with the teachings herein, the $^{19}$F spins in the decafluorobutane may be used as an HP agent. $^{19}$F spins in similarly configured halogens have been shown to have reasonably long $T_1$ relaxation times and $^{19}$F has a very low natural background in vivo.

In accordance with a further aspect, the beneficial agent may include a functional element disposed proximate the encapsulating medium, the functional element being adapted and configured to facilitate a beneficial result in use. The functional element may be selected from the group including proteins, mRNA, genetic probes, or any other material that binds preferentially to or otherwise seeks out biological activity and combinations thereof, among others. The functional element may be added to the beneficial agent prior to, during, or after hyperpolarization, as desired.

Figure 7A:
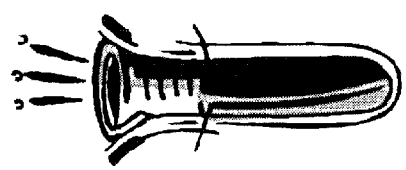
Figure 7B:
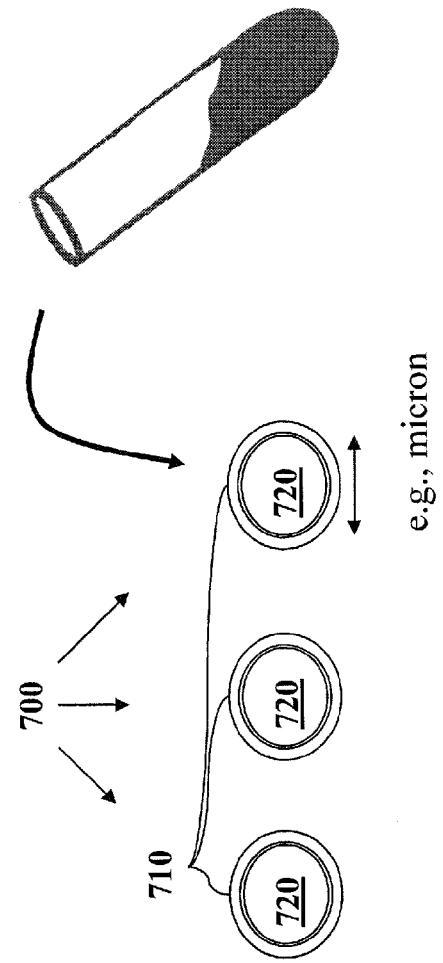
Figure 7D:
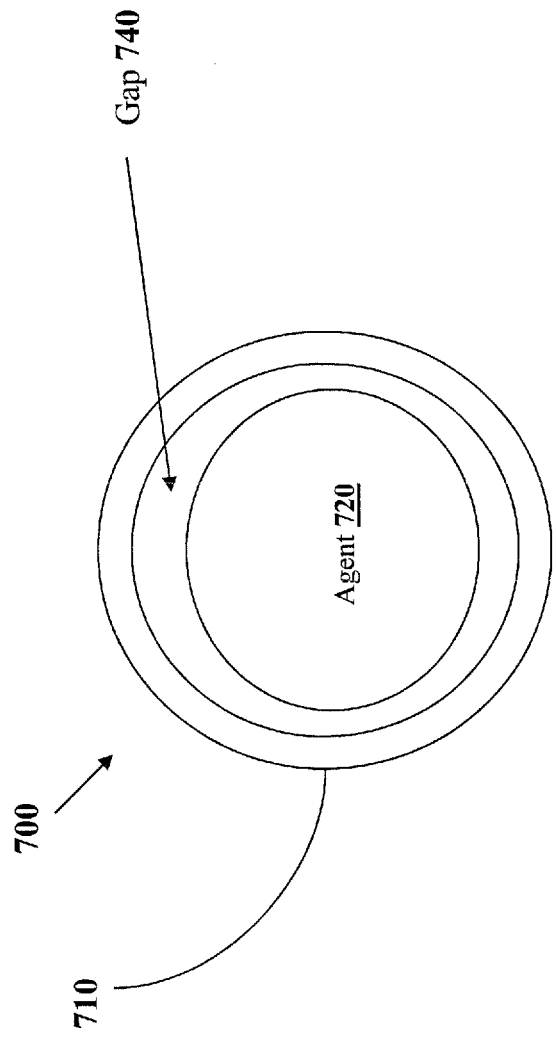
Figure 7E:
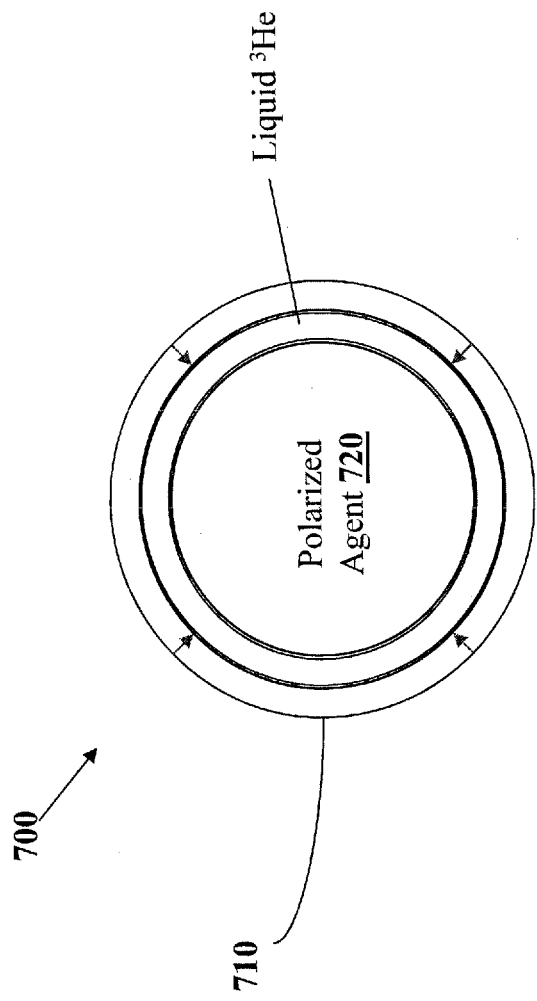
Figure 7F:
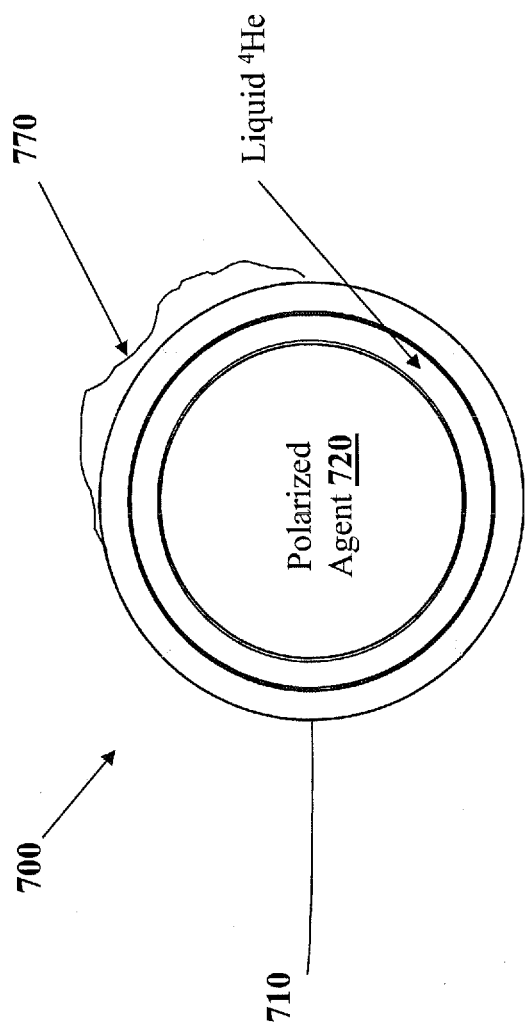

Thus, as will be appreciated, a coating 770 of a functional element may be provided on the surface of the beneficial agent 700 as depicted in FIG. 7(F). The functional element may be deposited directly on surface of shell 710, or may be caused to adhere to the surface of beneficial agent 700 according with a suitable surface treatment.

Another example of a composite material and beneficial agent 700 is a liposome containing hyperpolarized material. Liposomes may be used for drug delivery due to their unique properties. A liposome encapsulates a region on aqueous solution inside a hydrophobic membrane such that dissolved hydrophilic solutes can not readily pass through the lipids. Hydrophobic chemicals can be dissolved into the membrane, and in this way liposome can carry both hydrophobic molecules and hydrophilic molecules. To deliver the molecules to sites of action, the lipid bilayer can fuse with other bilayers such as the cell membrane, thus delivering the liposome contents. By making liposomes in a solution of DNA or drugs, (which would normally be unable to diffuse through the membrane), they can be (indiscriminately) delivered past the lipid bilayer.

Liposomes also have a natural ability to target cancer. The endothelial wall of all healthy human blood vessels are encapsulated by endothelial cells that are bound together by tight junctions. These tight junctions stop any large particle in the blood from leaking out of the vessel. Tumor vessels do not contain the same level of seal between cells and are diagnostically leaky. This ability is known as the Enhanced Permeability and Retention effect. Liposomes of certain sizes, typically less than 400 nm, can rapidly enter tumor sites from the blood, but are kept in the bloodstream by the endothelial wall in healthy tissue vasculature.

As will be appreciated, liposomes can be used as a vehicle to deliver hyperpolarized materials. For example, a hyperpolarized material (e.g., a hyperpolarized solvent or other mixture or material as described herein) may be incorporated into liposomes or material of the liposome itself may be caused to be hyperpolarized. These liposomes may be injected into a region of interest, such as a portion of a patient. The liposomes will seek out particular anatomy, and effectively deliver hyperpolarized materials to cells such where the contents of the liposome may be metabolized. For example, the metabolite products of the metabolism of hyperpolarized pyruvate delivered to a cancer cell by a liposome can accordingly be detected using NMR/MR techniques to determine the presence of a tumor. In the end, what happens is that the hyperpolarization from the pyruvate is transferred to the metabolites.

Moreover, it is possible to transfer hyperpolarization from a first material to a second material through a barrier, even when the two materials are not in direct physical contact. Specifically, if at least one of the two materials has a high "distant dipolar field" or "DDF", if desired, in accordance with the invention, one may hyperpolarize the contents of a body, such as a liposome or encapsulated material across the barrier (e.g., liposome body or encapsulating material) by taking advantage of this phenomenon.

Thus, in accordance with the invention, it is possible to administer a beneficial agent in the form of a hyperpolarized mixture such as a solution, suspension, emulsion, colloid or composite material, among others, to a region of interest, such as a patient. The mixture may be exposed to radiation of a frequency selected to excite nuclear spin transitions in the mixture. Next, it is possible to detect magnetic resonance signals from the mixture. As will be appreciated, optionally, it is possible to generate an image, dynamic flow data, diffusion data, perfusion data, physiological data, metabolic data or any other suitable data from the detected signals, and to transport such a material from a first location to a second location.

Thus, when delivered in vivo intravenously, for example, a layer 770 of functional element (or liposome as described herein) will tend to adhere to tissue that it is desired to image, such as tumors and the like. This will facilitate obtaining a strong MR signal from that region of interest, thus facilitating definitively localizing tissue of interest with great sensitivity.

By way of further example, the invention also provides a beneficial agent including a hyperpolarized core material surrounded by an encapsulating medium, wherein the hyperpolarized core material includes material selected from the group including (i) liquid material, (ii) solid material, (iii) gaseous material interspersed with a solid material, (iv) gaseous material interspersed with a liquid material, and combinations thereof. The encapsulating medium need not be porous in accordance with this aspect of the invention. Other aspects of the encapsulated medium described above are equally applicable to this embodiment of the invention. Accordingly, the encapsulating medium may be closed without pores, and the core material may be hyperpolarized, for example, by using DNP.

In further accordance with the invention, a kit for providing hyperpolarized material is provided.

For purposes of illustration and not limitation, as embodied herein, the kit includes at least one encapsulated material, similar to material 700 above. The encapsulated material includes a core material 720, which in turn includes a material having a relatively long spin-lattice relaxation time as described herein. The encapsulated material further includes an encapsulating medium 710 surrounding the core material. The kit also includes instructions for facilitating hyperpolarization of the encapsulated material.

The instructions for the kit preferably describe how to facilitate hyperpolarization of the encapsulated material. For example, the instructions may provide guidance for hyperpolarizing the core material using a quantum relaxation switch. By way of further example, the instructions of the kit may describe how to facilitate hyperpolarization of the encapsulated material by transferring hyperpolarization from a hyperpolarization carrier to the core material. In accordance with still a further aspect, the core material may be hyperpolarized using a technique selected from the group including (i) dynamic nuclear polarization, (ii) the Nuclear Overhauser effect, (ii) parahydrogen induced polarization, (iii) hyperpolarization using a quantum relaxation switch, and (iv) transferring hyperpolarization to molecules of the core material by exposing them to hyperpolarized nuclei of a previously hyperpolarized gas and combinations thereof.

In further accordance with the invention, a method of preparing and providing hyperpolarized encapsulated material is provided.

For purposes of illustration and not limitation, as embodied herein, in accordance with a first aspect, the method includes providing an encapsulated material, exposing the encapsulated material to a hyperpolarization carrier (and/or hyperpolarization facilitator, such as $^3$He in the context of QRS, which facilitates hyperpolarization but is not necessarily a hyperpolarization carrier itself), hyperpolarizing the hyperpolarization carrier, and transferring hyperpolarization from the hyperpolarization carrier to the encapsulated material.

The hyperpolarization carrier may be hyperpolarized using a technique selected from the group including (i) dynamic nuclear polarization, (ii) optical pumping, (iii) parahydrogen induced polarization, (iv) hyperpolarization using a quantum relaxation switch, (v) transferring hyperpolarization to molecules of the hyperpolarization carrier by exposing them to hyperpolarized nuclei of a previously hyperpolarized gas, (vi) the Nuclear Overhauser effect and combinations thereof.

The encapsulated material may include a porous surface portion to permit passage of the hyperpolarization carrier therethrough as described herein. As such, the hyperpolarization carrier may pass through the surface portion to the core portion. For example, the hyperpolarization carrier may include gaseous hyperpolarized xenon. In accordance with still a further aspect, the core portion may include material containing nuclei selected from the group including $^{13}$C, $^{15}$N, $^1$H, $^{31}$P, $^{19}$F, $^{29}$Si and combinations thereof.

The encapsulated material may further be cooled and/or subjected to a magnetic field to help induce and/or maintain hyperpolarization. Preferably, the encapsulated material is cooled to a temperature below about 100K, 10K or 1K. The magnetic field may have a maximum strength in excess of 10 mT, 1 T, or 10 T, for example.

If desired, the encapsulated material may be maintained at a low temperature and in a magnetic field for an extended period of time, such as between about one tenth of a second and about one week. The encapsulated hyperpolarized material may be transported in a container from a first location to a second location, as described herein. Prior to using the encapsulated hyperpolarized material, the temperature of the encapsulated material may first be increased such that substantial loss of hyperpolarization is avoided. The encapsulated hyperpolarized material may then be introduced into a region of interest to be analyzed. For example, magnetic resonance images of the region of interest may be generated. By way of further example, NMR spectra of an in vitro or in vivo sample may be analyzed.

It will be appreciated that the advantages of using encapsulated material is that the hyperpolarized core may be delivered to a desired region in vivo with minimum loss of hyperpolarization. In particular, by employing an encapsulating agent that excludes passage of oxygen or other depolarizing elements, the hyperpolarization of the encapsulated material may be extended as long as possible. Encapsulating materials that have already been approved for use in vivo are commercially available.

In accordance with a preferred embodiment, QRS is used to hyperpolarize the encapsulated material. Accordingly, the encapsulated material is exposed to $^3$He in lieu of a different material that has been previously hyperpolarized, such as a gas (e.g., $^{129}$Xe or others). Preferably, as embodied herein and as depicted in FIGS. 7(A)-7(F), the encapsulated material 700 has a porous outer shell portion 710 to permit passage of the $^3$He therethrough. However, it will be recognized that the capsule may have a surface portion that can be hyperpolarized, and a separate core portion need not be provided. However, the surface portion may nonetheless permit passage of a gas therethrough into a core portion of the encapsulated material, as described herein above.

In order to hyperpolarize the capsules and/or encapsulated material, as depicted in FIG. 7(C), at least one monolayer of $^3$He is formed on the structures to be hyperpolarized, for example, by pumping all other gas from a chamber 730 in which the beneficial agent 700 is contained. In accordance with one embodiment, the agent 720 may then freeze and contract away from polymer shell 710, leaving a gap 740 as depicted in FIG. 7(D). Layer 710 is preferably permeable to liquid $^3$He to permit a layer of $^3$He to form around the agent 720. The $^3$He relaxes nuclei in agent 720 to facilitate hyperpolarization condition. The agent 720 is then exposed to a high magnetic field at low temperatures for a time sufficient for nuclear hyperpolarization to occur.

As depicted in FIG. 7(F), the agent 700 may then be exposed to $^4$He to displace the $^3$He from the material, thus preserving the hyperpolarization of the material, but removing the $^3$He. In accordance with one embodiment, the hyperpolarized material may be maintained at a low temperature and/or in a magnetic field for an extended period of time. Maintaining the hyperpolarized material in such a manner facilitates storage and/or transport of the material, and minimizes loss of hyperpolarization from the material as described herein over significant periods of time. The hyperpolarized encapsulated material/capsules may be increased in temperature for use as described herein, if desired. Preferably, the temperature of the encapsulated material/capsules is increased in a manner that minimizes a substantial loss of the material's hyperpolarization.

It will be appreciated that the compositions methods and systems of the present invention, as described above and shown in the drawings, provide hyperpolarized materials in novel and useful forms, as well as facilitating the manufacture and delivery of hyperpolarized materials to end users.

It will be apparent to those skilled in the art that various modifications and variations can be made in the device and method and compositions of the present invention without departing from the spirit or scope of the invention. For example, it will be understood that any component in any solution, suspension, emulsion, colloid, composite material, or the like disclosed herein may be hyperpolarized. By way of further example, multiple components of such mixtures may be hyperpolarized. Moreover, it will be further appreciated that any such material may be hyperpolarized by way of at least: i) dynamic nuclear polarization, (ii) the Nuclear Overhauser effect, (ii) parahydrogen induced polarization, (iii) hyperpolarization using a brute force environment, most preferably in conjunction with a quantum relaxation switch, (iv) transferring hyperpolarization to molecules of the particles composed of various materials by exposing them to hyperpolarized nuclei of a previously hyperpolarized gas, and combinations thereof.

Mixing of components in the various mixtures disclosed herein may take place either before or after inducing hyperpolarization as described herein. Thus, it is intended that the present invention include modifications and variations that are within the scope of the appended claims and their equivalents.

What is claimed is:

1. A method of providing a suspension including a hyperpolarized beneficial agent, comprising:
    a) forming a plurality of capsules, each capsule including a core material comprising at least one material that is solid or liquid at standard conditions, surrounded by an encapsulating layer, wherein the encapsulating layer is porous to the passage of helium gas and excludes the passage of oxygen or other depolarizing elements;
    b) hyperpolarizing at least a portion of the core material to form a hyperpolarized beneficial agent, wherein hyperpolarization comprises the step of exposing the capsules to helium; and
    c) dispersing the hyperpolarized beneficial agent in a fluid medium.

2. The method of claim 1, wherein the encapsulating layer excludes the passage of oxygen.

3. The method of claim 1, wherein the fluid medium includes a physiologically tolerable liquid.

4. The method of claim 1, wherein the fluid medium includes a physiologically tolerable gas.

5. The method of claim 1, wherein the core material includes material that is a solid at standard conditions.

6. The method of claim 1, wherein the core material includes material that is a liquid at standard conditions.

7. The method of claim 1, wherein the core material includes $^{13}$C.

8. The method of claim 1, wherein the encapsulating layer includes solid material.

9. The method of claim 1, wherein the encapsulating layer includes a liposome having a lipid bilayer.

10. The method of claim 1, further comprising the step of forming an image of a region of interest where the hyperpolarized beneficial agent is present, wherein the image is formed by magnetic resonance imaging.

11. The method of claim 1, wherein the core material includes hyperpolarized pyruvate, and the method further comprises delivering the beneficial agent including the hyperpolarized pyruvate to a target cell, and detecting a hyperpolarized metabolite formed by the target cell from the hyperpolarized pyruvate, wherein the hyperpolarized metabolite is detected using magnetic resonance.

12. The method of claim 1, wherein the encapsulating layer includes a biologically derived medium.

13. The method of claim 1, wherein the encapsulating layer substantially maintains its structural integrity at temperatures below 100K.

14. The method of claim 1, wherein the capsules have an average diameter less than about 100 microns.

15. The method of claim 1, wherein the capsules have an average diameter less than about 10 microns.

16. The method of claim 1, wherein the capsules further include a functional element disposed proximate the encapsulating layer.

17. The method of claim 16, wherein the functional element includes a protein.

18. The method of claim 1, wherein the encapsulated material is transported from a first location where it is hyperpolarized to a second location remote from the first location in a storage vessel including an insulated Dewar disposed in a magnetic field created by the storage vessel.

19. The method of claim 1, wherein hyperpolarization is accomplished using a brute force environment in conjunction with a quantum relaxation switch employing $^3$He.

20. The method of claim 19, wherein the hyperpolarizing step includes decreasing the temperature of the core material to a temperature below about 100K.

21. The method of claim 19, wherein the hyperpolarizing step includes decreasing the temperature of the core material to a temperature below about 10K.

22. The method of claim 19, wherein the hyperpolarizing step includes decreasing the temperature of the core material to a temperature below about 1K.

* * * * *